(12) United States Patent
Bar-Or

(10) Patent No.: US 11,058,798 B2
(45) Date of Patent: *Jul. 13, 2021

(54) IMPLANTABLE MEDICAL DEVICES WITH INCREASED IMMUNE TOLERANCE, AND METHODS FOR MAKING AND IMPLANTING

(71) Applicant: AMPIO PHARMACEUTICALS, INC., Englewood, CO (US)

(72) Inventor: David Bar-Or, Englewood, CO (US)

(73) Assignee: Ampio Pharmaceuticals, Inc., Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/575,653

(22) Filed: Sep. 19, 2019

(65) Prior Publication Data

US 2020/0085999 A1   Mar. 19, 2020

Related U.S. Application Data

(63) Continuation of application No. 15/896,964, filed on Feb. 14, 2018, now Pat. No. 10,471,178, which is a continuation of application No. 14/350,617, filed as application No. PCT/US2012/059483 on Oct. 10, 2012, now Pat. No. 9,925,300.

(60) Provisional application No. 61/545,465, filed on Oct. 10, 2011.

(51) Int. Cl.
| | |
|---|---|
| *A61L 27/28* | (2006.01) |
| *A61L 29/16* | (2006.01) |
| *A61L 31/16* | (2006.01) |
| *A61K 31/495* | (2006.01) |
| *A61K 31/496* | (2006.01) |
| *A61L 27/54* | (2006.01) |

(52) U.S. Cl.
CPC ............ *A61L 27/28* (2013.01); *A61K 31/495* (2013.01); *A61K 31/496* (2013.01); *A61L 27/54* (2013.01); *A61L 29/16* (2013.01); *A61L 31/16* (2013.01); *A61L 2300/204* (2013.01); *A61L 2300/41* (2013.01); *A61L 2300/606* (2013.01); *F04C 2270/0421* (2013.01)

(58) Field of Classification Search
CPC .................................................. A61K 31/495
See application file for complete search history.

(56) References Cited

U.S. PATENT DOCUMENTS

| | | |
|---|---|---|
| 3,763,091 A | 10/1973 | Crescenzi et al. |
| 3,772,265 A | 11/1973 | Isowa et al. |
| 3,928,330 A | 12/1975 | Ramey et al. |
| 3,941,790 A | 3/1976 | Creighton |
| 3,976,773 A | 8/1976 | Curran |
| 4,006,261 A | 2/1977 | Pickenhagen et al. |
| 4,088,649 A | 5/1978 | Smith et al. |
| 4,205,057 A | 5/1980 | Whitaker |
| 4,289,759 A | 9/1981 | Heavner et al. |
| 4,312,987 A | 1/1982 | Beck |
| 4,331,595 A | 5/1982 | Heavner et al. |
| 4,661,500 A | 4/1987 | Rozencwaig |
| 4,694,061 A | 9/1987 | Pfeifer |
| 4,694,081 A | 9/1987 | Miller et al. |
| 4,771,056 A | 9/1988 | Rozencwaig |
| 4,806,538 A | 2/1989 | Shimazaki et al. |
| 4,886,796 A | 12/1989 | Eichner et al. |
| 4,940,709 A | 7/1990 | Shimazaki et al. |
| 4,992,552 A | 2/1991 | Hubbs et al. |
| 5,047,401 A | 9/1991 | Lipsky et al. |
| 5,144,073 A | 9/1992 | Hubbs |
| 5,238,938 A | 8/1993 | Tone et al. |
| 5,352,461 A | 10/1994 | Feldstein et al. |
| 5,358,938 A | 10/1994 | Cai et al. |
| 5,358,953 A | 10/1994 | Alker et al. |
| 5,418,218 A | 5/1995 | Wilber |
| 5,434,151 A | 7/1995 | Cai et al. |
| 5,463,083 A | 10/1995 | Biftu et al. |
| 5,503,852 A | 4/1996 | Steiner et al. |
| 5,512,544 A | 4/1996 | Wallach et al. |
| 5,538,993 A | 7/1996 | Mechoulam et al. |
| 5,543,402 A | 8/1996 | Bosies et al. |
| 5,543,503 A | 8/1996 | Chuntharapai et al. |
| 5,545,404 A | 8/1996 | Page |
| 5,550,132 A | 8/1996 | Benson et al. |
| 5,561,115 A | 10/1996 | Tenold |
| 5,578,323 A | 11/1996 | Milstein et al. |
| 5,589,501 A | 12/1996 | Carrera et al. |
| 5,648,486 A | 7/1997 | Cai et al. |

(Continued)

FOREIGN PATENT DOCUMENTS

| | | |
|---|---|---|
| CN | 1120439 | 4/1996 |
| CN | 101856345 | 10/2010 |

(Continued)

OTHER PUBLICATIONS

"A Prospective Phase I/II Study to Evaluate the Safety and Exploratory Efficacy of Three Intra-articular Injections of Ampion™ (4 ML) Administered Two Weeks Apart in Adults With Pain Due to Osteoarthritis of the Knee", U.S. National Library of Medicine, 2019 [retrieved on Sep. 15, 2020], 6 pages. Retrieved from: clinicaltrials.gov/ct2/history/NCT02184156?V_2=View#StudyPageTop.

Extended European Search Report for European Patent Application No. 20157236.9 dated Jul. 16, 2020, 10 pages.

"AP-007 Study to Evaluate Safety and Exploratory Efficacy of Three Intra-articular Injections of Ampion in the Knee of Adults With Pain Due to Osteoarthritis," U.S. National Library of Medicine, 2016 [retrieved on May 16, 2018], 7 pages. Retrieved from: clinicaltrials.gov/ct2/history/NCT02184156?V_2=View#StudyPageTop.

"CENTRICON Centrifugal Filter Devices User Guide," Millipore Corp., Mar. 2005, 23 pages.

(Continued)

*Primary Examiner* — Gina C Justice
(74) *Attorney, Agent, or Firm* — Sheridan Ross P.C.

(57) ABSTRACT

The present invention relates to the contacting of one or more surfaces of an implantable medical device with one or more diketopiperazines (DKPs).

20 Claims, No Drawings

(56) References Cited

U.S. PATENT DOCUMENTS

| | | |
|---|---|---|
| 5,665,714 A | 9/1997 | Paltauf et al. |
| 5,693,338 A | 12/1997 | Milstein |
| 5,700,804 A | 12/1997 | Collins et al. |
| 5,703,093 A | 12/1997 | Cai et al. |
| 5,741,809 A | 4/1998 | Biftu et al. |
| 5,750,530 A | 5/1998 | Bryans et al. |
| 5,750,565 A | 5/1998 | Cai et al. |
| 5,776,892 A | 7/1998 | Counts et al. |
| 5,780,503 A | 7/1998 | Biftu et al. |
| 5,792,776 A | 8/1998 | Biftu et al. |
| 5,811,241 A | 9/1998 | Goodfellow et al. |
| 5,817,751 A | 10/1998 | Szardenings et al. |
| 5,834,032 A | 11/1998 | Song |
| 5,843,950 A | 12/1998 | Tasaka et al. |
| 5,856,323 A | 1/1999 | Cai et al. |
| 5,877,174 A | 3/1999 | Ono et al. |
| 5,883,227 A | 3/1999 | Kline et al. |
| 5,886,152 A | 3/1999 | Nakatani et al. |
| 5,902,812 A | 5/1999 | Brocchini et al. |
| 5,919,785 A | 7/1999 | Dinsmore et al. |
| 5,925,626 A | 7/1999 | della Valle et al. |
| 5,932,112 A | 8/1999 | Browning, Jr. |
| 5,932,579 A | 8/1999 | Campbell et al. |
| 5,976,569 A | 11/1999 | Milstein |
| 5,985,581 A | 11/1999 | Nixon et al. |
| 5,990,112 A | 11/1999 | Campbell et al. |
| 6,034,057 A | 3/2000 | Dutta |
| 6,034,221 A | 3/2000 | Berezenko et al. |
| 6,060,452 A | 5/2000 | Green et al. |
| 6,090,780 A | 7/2000 | Prasad |
| 6,096,737 A | 8/2000 | Loder |
| 6,099,856 A | 8/2000 | Milstein et al. |
| 6,107,050 A | 8/2000 | Alkon et al. |
| 6,180,616 B1 | 1/2001 | Fukunaga |
| 6,222,029 B1 | 4/2001 | Edwards et al. |
| 6,248,363 B1 | 6/2001 | Patel et al. |
| 6,262,119 B1 | 7/2001 | Ferrante et al. |
| 6,265,535 B1 | 7/2001 | Greene et al. |
| 6,331,318 B1 | 12/2001 | Milstein et al. |
| 6,358,957 B1 | 3/2002 | Fukumoto et al. |
| 6,395,774 B1 | 5/2002 | Milstein |
| 6,441,172 B1 | 8/2002 | Nefzi et al. |
| 6,461,875 B1 | 10/2002 | Bar-Or et al. |
| 6,475,743 B1 | 11/2002 | Bar-Or et al. |
| 6,492,179 B1 | 12/2002 | Bar-Or et al. |
| 6,531,505 B2 | 3/2003 | Xu et al. |
| 6,541,224 B2 | 4/2003 | Yu et al. |
| 6,555,543 B2 | 4/2003 | Bar-Or et al. |
| 6,635,649 B2 | 10/2003 | Teng et al. |
| 6,677,473 B1 | 1/2004 | Madison et al. |
| 6,689,765 B2 | 2/2004 | Baroudy et al. |
| 6,815,214 B2 | 11/2004 | Boyce et al. |
| 6,930,112 B2 | 8/2005 | Weaver et al. |
| 6,967,202 B2 | 11/2005 | Rao et al. |
| 7,026,322 B2 | 4/2006 | Hayashi et al. |
| 7,175,844 B2 | 2/2007 | King |
| 7,276,534 B2 | 10/2007 | Milstein |
| 7,288,545 B2 | 10/2007 | Teng et al. |
| 7,332,153 B2 | 2/2008 | Bhatia et al. |
| 7,378,403 B2 | 5/2008 | Kozikowski et al. |
| 7,575,929 B2 | 8/2009 | Bar-Or et al. |
| 7,732,403 B2 | 6/2010 | Bar-Or et al. |
| 7,919,497 B2 | 4/2011 | Palladino et al. |
| 8,030,488 B2 | 10/2011 | Sviridov et al. |
| 8,067,425 B2 | 11/2011 | Brimble et al. |
| 8,183,209 B2 | 5/2012 | Bar-Or et al. |
| 8,198,407 B1 | 6/2012 | Burton et al. |
| 8,217,047 B2 | 7/2012 | Bar-Or |
| 8,268,830 B2 | 9/2012 | Bar-Or et al. |
| 8,314,106 B2 | 11/2012 | Kraft |
| 8,324,167 B2 | 12/2012 | Bar-Or et al. |
| 8,383,124 B2 | 2/2013 | Zheng |
| 8,440,696 B2 | 5/2013 | Bar-Or et al. |
| 8,455,517 B2 | 6/2013 | Bar-Or et al. |
| 8,507,496 B2 | 8/2013 | Bar-Or |
| 8,513,196 B2 | 8/2013 | Bar-Or et al. |
| 8,551,953 B2 | 10/2013 | Bar-Or et al. |
| 8,841,307 B2 | 9/2014 | Bar-Or et al. |
| 8,871,772 B2 | 10/2014 | Bar-Or |
| 8,916,568 B2 | 12/2014 | Bar-Or et al. |
| 8,962,568 B2 | 2/2015 | Bar-Or et al. |
| 8,969,308 B2 | 3/2015 | Bar-Or et al. |
| 8,980,834 B2 | 3/2015 | Bar-Or et al. |
| 9,034,878 B2 | 5/2015 | Bar-Or |
| 9,060,968 B2 | 6/2015 | Bar-Or et al. |
| 9,522,893 B2 | 12/2016 | Bar-Or |
| 9,561,226 B2 | 2/2017 | Bar-Or et al. |
| 9,623,072 B2 | 4/2017 | Bar-Or et al. |
| 9,707,227 B2 | 7/2017 | Bar-Or et al. |
| 9,730,924 B2 | 8/2017 | Bar-Or et al. |
| 9,808,454 B2 | 11/2017 | Bar-Or et al. |
| 9,925,300 B2 | 3/2018 | Bar-Or |
| 9,956,217 B2 | 5/2018 | Bar-Or |
| 10,251,930 B2 | 4/2019 | Bar-Or et al. |
| 10,342,793 B2 | 7/2019 | Bar-Or |
| 10,471,178 B2 | 11/2019 | Bar-Or |
| 2002/0123505 A1 | 9/2002 | Mollison et al. |
| 2003/0119750 A1 | 6/2003 | Demuth et al. |
| 2003/0153575 A1 | 8/2003 | Orme et al. |
| 2003/0157030 A1 | 8/2003 | Davis et al. |
| 2003/0187226 A1 | 10/2003 | Goddey et al. |
| 2003/0203915 A1 | 10/2003 | Fang et al. |
| 2004/0024180 A1 | 2/2004 | Drauz et al. |
| 2004/0038865 A1 | 2/2004 | Gelber et al. |
| 2004/0063654 A1 | 4/2004 | Davis et al. |
| 2005/0096323 A1 | 5/2005 | Cheng et al. |
| 2005/0249681 A1 | 11/2005 | Heidenfelder et al. |
| 2007/0060508 A1 | 3/2007 | Haberl et al. |
| 2007/0208087 A1 | 9/2007 | Sanders et al. |
| 2008/0009507 A1 | 1/2008 | Cosford et al. |
| 2008/0017576 A1 | 1/2008 | Belfort et al. |
| 2008/0260838 A1 | 10/2008 | Hokenson et al. |
| 2009/0038416 A1 | 2/2009 | Bonner |
| 2010/0042206 A1 | 2/2010 | Yadav et al. |
| 2010/0120056 A1 | 5/2010 | Bar-Or et al. |
| 2010/0190696 A1 | 7/2010 | Bar-Or et al. |
| 2012/0058934 A1 | 3/2012 | Bar-Or |
| 2012/0094918 A1 | 4/2012 | Bar-Or et al. |
| 2012/0220530 A1 | 8/2012 | Plumridge et al. |
| 2013/0079284 A1 | 3/2013 | Bar-Or et al. |
| 2014/0294738 A1 | 10/2014 | Bar-Or |
| 2015/0366932 A1 | 12/2015 | Bar-Or |
| 2016/0367644 A1 | 12/2016 | Bar-Or et al. |
| 2017/0209433 A1 | 7/2017 | Bar-Or et al. |
| 2018/0140598 A1 | 5/2018 | Bar-Or et al. |
| 2019/0314448 A1 | 10/2019 | Bar-Or et al. |
| 2020/0000800 A1 | 1/2020 | Bar-Or |

FOREIGN PATENT DOCUMENTS

| | | |
|---|---|---|
| CS | 254868 | 6/1987 |
| CZ | 2827.94 | 4/1996 |
| CZ | 280726 | 4/1996 |
| CZ | 2000-2680 | 7/2000 |
| CZ | 2000-2681 | 7/2000 |
| DE | 19937721 | 2/2001 |
| EP | 0043219 | 1/1982 |
| EP | 0214557 | 3/1987 |
| EP | 0216746 | 4/1987 |
| EP | 0220958 | 5/1987 |
| EP | 0493812 | 7/1992 |
| EP | 0557388 | 9/1993 |
| EP | 0610943 | 8/1994 |
| EP | 0655060 | 5/1995 |
| EP | 0835660 | 4/1998 |
| EP | 0939124 | 9/1999 |
| EP | 1445323 | 8/2004 |
| FR | 2717484 | 9/1995 |
| GB | 2263109 | 7/1993 |
| GB | 2372740 | 9/2002 |
| JP | S52-25019 | 2/1977 |
| JP | S59-73574 | 4/1984 |
| JP | S61-112060 | 5/1986 |
| JP | S62-036331 | 2/1987 |

(56) References Cited

FOREIGN PATENT DOCUMENTS

| | | |
|---|---|---|
| JP | S63-290868 | 11/1988 |
| JP | H01-013075 | 1/1989 |
| JP | 3176478 | 7/1991 |
| JP | H05-163148 | 6/1993 |
| JP | H07-247474 | 9/1995 |
| JP | H08-277203 | 10/1996 |
| JP | H10-226615 | 8/1998 |
| JP | H10-245315 | 9/1998 |
| JP | H11-504509 | 4/1999 |
| JP | 2000-327575 | 11/2000 |
| JP | 2001-055340 | 2/2001 |
| JP | 2002-527753 | 8/2002 |
| JP | 2008-505084 | 2/2008 |
| JP | 2009-508658 | 3/2009 |
| JP | 2010-508971 | 3/2010 |
| JP | 2011-507609 | 3/2011 |
| NZ | 218088 | 1/1989 |
| NZ | 335544 | 8/2001 |
| RU | 2112242 | 5/1998 |
| RU | 2125728 | 1/1999 |
| RU | 2128840 | 4/1999 |
| WO | WO 91/14378 | 10/1991 |
| WO | WO 93/08815 | 5/1993 |
| WO | WO 94/04512 | 3/1994 |
| WO | WO 94/04513 | 3/1994 |
| WO | WO 94/04537 | 3/1994 |
| WO | WO 94/20063 | 9/1994 |
| WO | WO 95/03054 | 2/1995 |
| WO | WO 95/18610 | 7/1995 |
| WO | WO 96/00212 | 1/1996 |
| WO | WO 96/00391 | 1/1996 |
| WO | WO 96/10396 | 4/1996 |
| WO | WO 96/14317 | 5/1996 |
| WO | WO 96/32478 | 10/1996 |
| WO | WO 97/12625 | 4/1997 |
| WO | WO 97/36888 | 10/1997 |
| WO | WO 97/38011 | 10/1997 |
| WO | WO 97/48685 | 12/1997 |
| WO | WO 98/09968 | 3/1998 |
| WO | WO 98/40748 | 9/1998 |
| WO | WO 99/40931 | 8/1999 |
| WO | WO 99/49865 | 10/1999 |
| WO | WO 99/51256 | 10/1999 |
| WO | WO 99/51720 | 10/1999 |
| WO | WO 00/20454 | 4/2000 |
| WO | WO 00/20840 | 4/2000 |
| WO | WO 00/22439 | 4/2000 |
| WO | WO 00/43000 | 7/2000 |
| WO | WO 00/057187 | 9/2000 |
| WO | WO 01/34586 | 5/2001 |
| WO | WO 01/64241 | 9/2001 |
| WO | WO 01/91713 | 12/2001 |
| WO | WO 02/011676 | 2/2002 |
| WO | WO 02/012201 | 2/2002 |
| WO | WO 02/059604 | 8/2002 |
| WO | WO 02/062797 | 8/2002 |
| WO | WO 02/083667 | 10/2002 |
| WO | WO 02/089738 | 11/2002 |
| WO | WO 03/032809 | 4/2003 |
| WO | WO 03/045395 | 6/2003 |
| WO | WO 2004/005292 | 1/2004 |
| WO | WO 2004/034060 | 4/2004 |
| WO | WO 2004/048345 | 6/2004 |
| WO | WO 2004/054498 | 7/2004 |
| WO | WO 2004/103304 | 12/2004 |
| WO | WO 2005/011699 | 2/2005 |
| WO | WO 2006/023943 | 3/2006 |
| WO | WO 2007/098500 | 8/2007 |
| WO | WO 2007/121411 | 10/2007 |
| WO | WO 2007/149730 | 12/2007 |
| WO | WO 2008/008357 | 1/2008 |
| WO | WO 2009/009793 | 1/2009 |
| WO | WO 2009/032651 | 3/2009 |
| WO | WO 2009/042193 | 4/2009 |
| WO | WO 2010/102148 | 9/2010 |
| WO | WO 2012/033789 | 3/2012 |
| WO | WO 2012/174472 | 12/2012 |

OTHER PUBLICATIONS

Cytokines and Autoimmune Diseases, edited by Kuchroo, et al., 2002, Humana Press Inc., Totowa, NJ, pp. 3-23, 389-406.
Cytokines and Autoimmune Diseases, edited by Kuchroo, et al., 2002, Humana Press Inc., Totowa, NJ, pp. 5, 11, and 391.
Database WPI Section Ch, Week 199844 Derwent Publications Ltd., London, GB; AN 1998-515050 XP002369751 & JP 10 226615 A (POLA CHEM IND INC) Aug. 25, 1998 (Aug. 25, 1998).
"Diabetic Retinopathy—What you should know," National Institutes of Health, 2003, NIH Publication No. 06-2171, 24 pages.
"Disposable PD-10 Desalting Columns," GE Healthcare Life Sciences, downloaded Nov. 1, 2011, 2 pages.
"Desalting and buffer exchange with Sephadex® G-25," Amersham Biosciences, downloaded from www.gelifesciences.com on Jan. 8, 2013, 8 pages.
"Human Albumin," Sigma downloaded from www.sigmaaldrich.com on Jan. 8, 2013, 1 page.
Online Medical Dictionary definition of albumin, medical-dictionary.thefreedictionary.com/albumin, downloaded Nov. 1, 2011, 4 pages.
The Cytokine Handbook, edited by Thomson and Lotze, 4th edition, 2003 Academic Press, vol. I, London, UK, pp. 169, 186, 187, 467, 570, 571, 838, 839, 1189-1193, 1197-1200.
The Cytokine Handbook, edited by Thomson and Lotze, 4th edition, 2003 Academic Press, vol. II, London, UK, pp. 838-860 and 1189-1211.
The Cytokine Handbook, edited by Thomson and Lotze, 4th edition, 2003 Academic Press, vol. I, London, UK, pp. 167-199, 456-474, 567-601.
The Dictionary of Immunology, Fourth Edition, Edited by Herbert et al., 1995, pp. 51-52 and 69.
"Tryprostatin A, Aspergillus fumigates," available at www.emdbiosciences.com/Products/ProductDisplay.asp?catno=649305&, printed on Jun. 21, 2006, 1 page.
Abraha et al., "C-terminal inhibition of tau assembly in vitro and in Alzheimer's disease," Journal of Cell Science, 2000, vol. 113, pp. 3737-3745.
Acharya et al., "Solid-phase synthesis of substituted imidazoline-tethered 2,3-diketopiperazines, cyclic ureas, and cyclic thioureas," J Comb Chem, Nov.-Dec. 2001, vol. 3(6), pp. 612-623.
Adorini, L., "Selective immunointervention in autoimmune diseases: lessons from multiple sclerosis," J Chemother, Jun. 2001, vol. 13(3), pp. 219-234 (Abstract Only Provided).
Akiyama et al., "Inflammation and Alzheimer's disease," Neurobiol Aging, 2000, vol. 21, pp. 383-421.
Albert et al., "ABT-491, a highly potent and selective PAF antagonist, inhibits nasal vascular permeability associated with experimental allergic rhinitis in Brown Norway rats," Inflamm. Res., 1997, Supplement 2, pp. S133-S134.
Alvarez et al., "Isolation and Structure Elucidation of Two New Calpain Inhibitors from Streptomyces Griseus," J. Antibiotics, Nov. 1994, vol. 47(11), pp. 1195-1201.
Andreasen et al., "Cerebrospinal fluid beta-amyloid (1-42) in Alzheimer disease: differences between early- and late-onset Alzheimer disease and stability during the course of disease," Arch. Neurol., Jun. 1999, vol. 56(6), pp. 673-680.
Arbabi et al., "Priming Interleukin 8 Production: Role of Platelet-Activating Factor and p38," Arch Surg., Dec. 1999, vol. 134(12), pp. 1348-1353.
Ashwood et al. "Is autism an autoimmune disease?" Autoimmunity Reviews, Nov. 2004, vol. 3, No. 7-8, pp. 557-562.
Au et al., "Effect of PDE4 Inhibitors on Zymosan-Induced IL-8 Release From Human Neutrophils: Synergism with Prostanoids and Salbutamol," Br. J. Pharmacol, 1998, vol. 123, pp. 1260-1266.
Bagaria et al., "Cyclo(L-leucyl-alpha,beta-dehydrophenylalanine): the first diketopiperazine containing an alpha,beta-dehydrophenylalanine residue," Acta Crystallogr C., Mar. 2005, vol. 61(Pt 3), pp. 174-176, Epub Feb. 28, 2005.

(56) References Cited

OTHER PUBLICATIONS

Baig et al., "High Performance Liquid Chromatography as a Tool in the Definition of Abnormalities in Monamine and Tryptophan Metabolites in Cerebrospinal Fluid from Patients with Neurological Disorders," Biomed Chromatogr 1991, 5(3):108-112 (Abstract Only Provided).
Balk, "Lesson 24, vol. 12—ARDS: Pathophysiology of SIRS and MODS" www.chestnet.org/education/pccu/vol12/ lesson24.html, pp. 1-19, printed Jul. 20, 2000.
Banks et al., "Radioactively Iodinated Cyclo(His-Pro) Crosses the Blood-Brain Barrier and Reverses Ethanol-Induced Narcosis," Am J Physiol, May 1993, vol. 264(5 Pt. 1), pp. E723-E729 (Abstract Only Provided).
Bar-Or et al. "Commercial human albumin preparations for clinical use are immunosuppressive in vitro," Critical Care Medicine, Jun. 2006, vol. 34, No. 6, pp. 1707-1712.
Bar-Or et al., "An Analog of the Human Albumin N-Terminus (Asp-Ala-His-Lys) Prevents Formation of Copper-Induced Reactive Oxygen Species," Biochemical and Biophysical Research Communications, 2001, vol. 284(3), pp. 856-862.
Bar-Or et al., "Potential Plasma Surrogate Biomakers for CNS Demyelinating Processes," 19th Congress of the European Committee for Treatment and Research in Multiple Sclerosis Meeting; Sep. 17-20, 2003; 2 pp. (Abstract first distributed at the meeting; attached is poster presented at meeting).
Barrow et al., WIN 64821, a New Competitive Antagonist to Substance P, Isolated from an *Aspergillus* Species: Structure Determination and Solution Conformation, J. Org. Chem., 1993, vol. 58, pp. 6016-6021.
Battersby et al., "Diketopiperazine Formation and N-Terminal Degradation in Recombinant Human Growth Hormone," Int. J. Pept. Protein Res, Sep. 1994, vol. 44(3), pp. 215-222 (Abstract Only Provided).
Berman et al., "Psoriasis," PubMed Health, reviewed Nov. 22, 2011, available at www.ncbi.nlm.nih.gov/pubmedhealth/PMH0001470/?report=printable.
Berry et al., "Inhibition of Tau Polymerization by its Carboxy-Terminal Caspase Cleavage Fragment," Biochemistry, 2003, vol. 42, pp. 8325-8331.
Bhargava et al., "Inhibition of Neuroleptic-Induced Dopamine Receptor Supersensitivity by Cyclo (Leu-Gly)," Pharmacol Biochem Behav, Nov. 1980, vol. 13(5), pp. 633-636 (Abstract Only Provided).
Bhargava, "Antagonism of ketamine-induced anesthesia and hypothermia by thyrotropin releasing hormone and cyclo (His-Pro)," Neuropharmacology, 1981, vol. 20(7), pp. 699-702.
Bhargava, "Inhibition of abstinence syndrome in opiate dependent mice by cyclo (His-Pro)," Life Sci, 1981, vol. 28(11), pp. 1261-1267.
Bhargava, "The effect of melanotrophin release inhibiting factor (MIF) and cyclo (Leu-Gly) on the tolerance to morphine-induced antinociception in the rat: a dose-response study," Br J Pharmacol, Apr. 1981, vol. 72(4) (Abstract Only Provided).
Bhargava, "The effects of thyrotropin releasing hormone and histidyl-proline diketopiperazine on delta-9-tetrahydrocannabinol-induced hypothermia," Life Sci, 1980, vol. 26(11), pp. 845-850.
Bielekova et al., "Development of biomarkers in multiple sclerosis," Brain, Jul. 2004, vol. 127(Pt 7), pp. 1463-1478, Epub Jun. 4, 2004.
Binisti et al., "Structure-Activity Relationships in Platelet Activating Factor," J. Lipid Mediat. Cell Signal, Jan. 1997, vol. 15(2), pp. 125-144 (Abstract Only Provided).
Blazickova et al., "Immunomodulatory Characteristics of Synthetic Cyclic Dipeptides," Int. J. Immunotherapy, 1994, vol. 10(3), pp. 89-93.
Borthwick, "2,5-Diketopiperazines: Synthesis, Reactions, Medicinal Chemistry, and Bioactive Natural Products," Chemical Reviews, 2012, vol. 112, Iss. 7, pp. 3641-3716.
Bowden et al., "Re-evaluation of histidyl-proline diketopiperazine [cyclo (His-Pro)] effects on food intake in the rate," Pharmacol. Biochem. Behav., Feb. 1988, vol. 29(2), pp. 357-363 (Abstract Only Provided).
Brauns et al., "Selected cyclic dipeptides inhibit cancer cell growth and induce apoptosis in HT-29 colon cancer cells," Anticancer Research, 2004, vol. 24, pp. 1713-1720.
Bressan et al., "Coordination chemistry of peptides. Part II. Crystal structure of cyclo-L-methionylglycine and studies of metal complexation," Int J Pept Protein Res, Apr. 1982, vol. 19(4) (Abstract Only Provided).
Bresser et al., "T-Cell Activation in the Lungs of Patients With Systemic Sclerosis and Its Relation With Pulmonary Fibrosis," Chest, Jul. 2001, 6 pages.
Brown et al., "Anti-VEGF Agents in the Treatment of Neovascular Age-related Macular Degeneration: Applying Clinical Trial Results to the Treatment of Everyday Patients," American Journal of Opthalmology, 2007, vol. 144, Iss. 4, pp. 627-637.
Bunn, "Early detection of lung cancer using serum RNA or DNA markers: ready for "prime time" or for validation?," J Clin Oncol., Nov. 1, 2003, vol. 21(21), pp. 3891-3893.
Caballero et al., "Brief synthesis of the cell cycle inhibitor tryprostatin B and its alanine analogue," Fourth International Electronic conference of Synthetic Organic Chemistry (ECXOC-4), Sep. 1-13, 2000, 4 pages, available at pages.unibas.ch/mdpi/eecxoc-4/c0023/c0023.htm.
Caballero et al., "Brief total synthesis of the cell cycle inhibitor tryprostatin B and related preparation of its alanine analogue," J Org Chem, Sep. 5, 2003, vol. 68(18) (Abstract Only Provided).
Carlton et al., "Attenuation of alcohol-induced hypothermia by cycle (His-Pro) and its analogs," Neuropeptides, Jun. 1995, vol. 28(6), pp. 351-355 (Abstract Only Provided).
Chan, "Chapter 9: Transplant Rejection and Its Treatment," Atlas of Diseases of the Kidney, vol. 5, (Ed.Henrich et al.), Wiley-Blackwell, 1999, pp. 9.1-9.13.
Chan et al., "Site-Specific N-Terminal Auto-Degradation of Human Serum Albumin," Eur. J. Biochem., 1995, vol. 227, pp. 524-528.
Chen et al., "Up-regulation of Platelet-activating Factor Receptors in Lung and Alveolar Macrophages in the Bleomycin-Hamster Model of Pulmonary Fibrosis," J. Pharmacol. Exp. Ther., 1997, vol. 280(3), pp. 1219-1227.
Cho et al., "Contribution of Natural Inhibitors to the Understanding of the PI3K/PDK1/PKB Pathway in the Insulin-mediated Intracellular Signaling Cascade," Int. J. Mol. Sci., 2008, vol. 9, pp. 2217-2230.
Ciarkowski et al., "Conformation of cyclo-(D-phenylalanyl-trans-4-fluoro-D-prolyl)," Int. J. Pept. Protein Res., vol. 36, Sep. 1990, pp. 285-291.
Clark et al., "Roquefortine E, a Diketopiperazine from an Australian Isolate of Gymnoascus reessii," J. Nat. Prod., 2005, vol. 68(11), p. 1661-1664 (Abstract Only Provided).
Cody et al., "The design of potent and selective inhibitors of thrombin utilizing a piperazinedione template: part 2," Bioorg Med Chem Lett, Sep. 6, 1999, vol. 9(17), pp. 2503-2508.
Coggins et al., "High Affinity Specific Binding of the Thyrotrophin Releasing Hormone Metabolite Histidylproline to Rat Brain Membranes," Neuropeptides, Jan. 1987, vol. 9(1), pp. 83-91 (Abstract Only Provided).
Costa et al., "Aggregation of features of the metabolic syndrome is associated with increased prevalence of chronic complications in Type 2 diabetes," Diabetic Medicine, 2004, vol. 21, Iss. 3, 252-255.
Couladouros et al., "Solid-phase total synthesis of (−)-Phenylhistine and (−)-Aurantiamine. Synthesis of a diverse dehydro-2,5-diketopiperazine library. Part II," Mol Divers., 2005, vol. 9(1-3), pp. 111-121.
Crowe et al., "The N Terminal Region of Human Tau is Present in Alzheimer's Disease Protein A68 and is Incorporated into Paired Helical Filaments," American Journal of Pathology, 1991, vol. 139(6), pp. 1463-1470.
Cruse et al., "Illustrated Dictionary of Immunology" Second Edition, 2003, pp. 192, 260, 530-531.
Cui et al., "Novel Mammalian Cell Cycle Inhibitors, Tryprostatins A, B and Other Diketopiperazines Produced by Aspergillus fumigatus

(56) References Cited

OTHER PUBLICATIONS

II. Physico-chemical properties and Structures," The Journal of Antibiotics, Jun. 1996, pp. 534-540.
D'Alagni et al. "Effect of Urea on the Optical Rotatory Dispersion of Diketopiperazines of l-Serine, l-Alanine, l-Lysine, l-Valine, and l-Valylglycine." The Journal of Biological Chemistry, Nov. 10, 1969, vol. 244, No. 21, pp. 5843-5848.
Davidson et al., "Autoimmune Diseases," N. Engl. J. Med, 2001, vol. 345(5), pp. 340-350.
De La Cruz et al, "Effect of WEB 2086-BS, an antagonist of platelet-activating factor receptors, on retinal vascularity in diabetic rats," European Journal of Pharmacology, 1998, vol. 360, Iss. 1, pp. 37-42.
Degrassi et al., "Plant Growth-Promoting Pseudomonas putida WCS358 Produces and Secretes Four Cyclic Dipeptides: Cross-Talk with Quorum Sensing Bacterial Sensors," Current Microbiology, 2002, vol. 45, pp. 250-254.
Del Fresno et al. "Solid-phase synthesis of diketopiperazines, useful scaffolds for combinatorial chemistry," Tetrahedron Letters, 1998, vol. 39, Iss. 17, pp. 2639-2642.
Denault et al., "Transcriptional activation of the interleukin-8 gene by platelet-activating factor in human peripheral blood monocytes," Immunology, 1997, vol. 91, pp. 297-302.
Diamanti et al., "Distribution and Characterization of Cyclo (His-Pro)-like Immunoreactivity in the Human Gastrointestinal Tract," Neuropeptides, Mar. 1985, vol. 6(1):21-5 (Abstract Only Provided).
Dirr, K. et al., "The transformation of arginine into citrulline," Z. Physiol. Chem., 1935, vol. 237, pp. 121-130.
Duntas et al., "A Fast Protein Liquid Chromatography (FPLC) Method for Study of Thyrotropin-releasing Hormone (TRH) and its metabolite Histidyl-Proline Diketopiperazine (CHP) in Human Blood: Degradation in Liver and Pancreatic Diseases," Neuropeptides, 1993, vol. 25(6), pp. 357-361 (Abstract Only Provided).
Esposito et al., "The Solution Structure of the C-Terminal Segment of Tau Protein," Journal of Peptide Science, 2000, vol. 6, pp. 550-559.
Evans et al. "Metabolic effects of platelet-activating factor in rats in vivo: Stimulation of hepatic glycogenolysis and lipogenesis." Biochemical Journal, Jul. 1990, vol. 269, No. 1, pp. 269-272.
Faden et al., "Neuroprotective and nootropic actions of a novel cyclized dipeptide after controlled cortical impact injury in mice." J. Cerebral Blood Flow & Metabolism, 2003, vol. 23, pp. 355-363.
Faden et al., "Novel diketopiperazine enhances motor and cognitive recovery after traumatic brain injury in rats and shows neuroprotection in vitro and in vivo," J. Cerebral Blood Flow & Metabolism, 2003, vol. 23, pp. 342-354.
Faden et al., "Novel neuroprotective Tripeptides and Dipeptides," Ann. N.Y. Acad. Sci, 2005, vol. 1053, pp. 472-481.
Faden et al., "Novel small peptides with neuroprotective and nootropic properties," J. Alzheimer's Dis, 2004, vol. 6, pp. S93-S97.
Faden et al., "Novel TRH analog improves motor and cognitive recovery after traumatic brain injury in rodents," Am J Physiol, Oct. 1999, vol. 277(4 Pt 2), pp. R1196-R1204.
Falorni et al. "Chiral ligands containing heteroatoms. 11. Optically active 2-hydroxymethyl piperazines as catalysts in the enantioselective addition of diethylzinc to benzaldehyde," Tetrahedron: Asymmetry, 1993, vol. 4, Iss. 11, pp. 2389-2398.
Falorni et al. "Chiral ligands containing heteroatoms. 11. Optically active 2-hydroxymethyl piperazines as catalysts in the enantioselective addition of diethylzinc to benzaldehyde," Tetrahedron: Asymmetry, 1993, vol. 4, Iss. 11, pp. 2389-2398. (Abstract and Graphic only).
Fdhila et al., "dd-diketopiperazines: antibiotics active against Vibrio anguillarum isolated form marine bacteria associated with cultures of Pecten maximus" J Nat Prod, Oct. 2003, vol. 66(10) (Abstract Only Provided).
Fischer, "Diketopiperazines in Peptide and Combinatorial Chemistry," Journal of Peptide Science, 2003, vol. 9, pp. 9-35.

Folkes et al., "Synthesis and in vitro evaluation of a series of diketopiperazine inhibitors of plasminogen activator inhibitor-1," Bioorg Med Chem Lett, Oct. 2001, vol. 11(19), pp. 2589-2592 (Abstract Only Provided).
Fragner et al., "A New Biological Contribution of Cyclo(His-Pro) to the Peripheral Inhibition of Pancreatic Secretion," Am J Physiol, Dec. 1997, vol. 273(6 Pt. 1), pp. E1127-E1132 (Abstract Only Provided).
Franklin et al., "Association between occupation and knee and hip replacement due to osteoarthritis: a case-control study," Arthritis Research & Therapy, 2010, vol. 12, R102, 9 pages.
Gamblin et al., "Tau Polymerization: Role of the Amino Terminus," Biochemistry, 2003, vol. 42(7), pp. 2252-2257.
Garcia-Sierra et al., "Conformational Changes and Truncation of Tau Protein during Tangle Evolution in Alzheimer's Disease," Journal of Alzheimer's Disease, 2003, vol. 5, pp. 65-77.
Gomez et al., "Low-Dose Dopamine Agonist Administration Blocks Vascular Endothelial Growth Factor (VEGF)-Mediated Vascular Hyperpermeability without Altering VEGF Receptor 2-Dependent Luteal Angiogenesis in a Rat Ovarian Hyperstimulation Model," Endocrinology, 2006, vol. 147, No. 11, pp. 5400-5411.
Goolcharran et al., "Comparison of the Rates of Deamidation, Diketopiperazine Formation and Oxidation in Recombinant Human Vascular Endothelial Growth Factor and Model Peptides," AAPS PharmSci, 2000 vol. 2(1), p. E5 (Abstract Only Provided).
Gorbitz "Crystal and Molecular Structure of cyclo-L-Aspartyl-L-alanyl (3,6-Dioxo-5-methyl-2-piperazineacetic acid)" Acta Chemica Scandinavica B, 1987, vol. 41, pp. 83-86.
Gorbitz, "Crystal and molecular structures of the isomeric dipeptides alpha-L-aspartyl-L-alanine and beta-L-aspartyl-L-alanine," Acta Chem Scand B., vol. 41(9), Oct. 1987, pp. 679-685.
Gordon et al, "Reductive Alkylation on a Solid Phase: Synthesis of a Piperazinedione Combinatorial Library," Bioorganic & Medicinal Chemistry Letters, 1995, vol. 5, No. 1, p. 47-50.
Gountopoulou et al. "TNFα is a potent inducer of platelet-activating factor synthesis in adipocytes but not in preadipocytes. Differential regulation by PI3K." Cytokine, Jan. 2008, vol. 41, No. 2 p. 174-181, (Abstract Only).
Graz et al "Cyclic Dipeptides in the Induction of Maturation for Cancer Therapy," J. Pharm. Pharmacol., 2000, vol. 52, pp. 75-82.
Graz et al., "Mechanism of a anti-fungal action of selected cyclic dipeptides," Pharmazie, Nov. 2001, vol. 56(11), pp. 900-901.
Gross et al., "Regulation of Interleukin-8 Production in a Human Colon Epithelial Cell Line (HT-29)," Gastroenterology, 1995, vol. 108, pp. 653-661.
Grubek-Jaworska et al., "CD4/CD8 lymphocytes in BALF during the efferent phase of lung delayed-type hypersensitivity reaction induced by single antigen inhalation," Med Sci Monit, Sep.-Oct. 2001, vol. 7(5), pp. 878-883 (Abstract Only Provided).
Gu et al., "Diketopiperazine Formation, Hydrolysis, and Epimerization of the New Dipeptide Angiotensin-Converting Enzyme Inhibitor RS-10085," Pharm Res, 1987, vol. 4(5), pp. 392-397 (Abstract Only Provided).
Gudasheva et al., "Anxiolytic activity of endogenous nootropic dipeptide cycloprolylglycine in elevated plus-maze test," Bull Exp Biol Med, May 2001, vol. 131(5) (Abstract Only Provided).
Gudasheva et al., "Identification of a novel endogenous memory facilitating cyclic dipeptide cyclo-prolylglycine in rat brain," FEBS Lett, Aug. 5, 1996, vol. 391(1-2) (Abstract Only Provided).
Guerra et al., "PEGylation Prevents the N-Terminal Degradation of Megakaryocyte Growth and Development Factor," Pharm Res, 1998, vol. 15(12), pp. 1822-1827 (Abstract Only Provided).
Gustafson, "Adipose Tissue, Inflammation and Atherosclerosis," J. Atheroscler. Thromb., Apr. 30, 2010, vol. 17(4), pp. 332-341.
Hansel et al. "Metabolic Syndrome Is Associated with Elevated Oxidative Stress and Dysfunctional Dense High-Density Lipoprotein Particles Displaying Impaired Antioxidative Activity." The Journal of Clinical Endocrinology & Metabolism, Oct. 2004, vol. 89, No. 10, pp. 4963-4971.
Harada et al., "Essential involvement of interleukin-8 (IL-8) in acute inflammation," Journal of Leukocyte Biology, 1994, vol. 56, Iss. 5, pp. 559-564.

(56) References Cited

OTHER PUBLICATIONS

Hasegawa et al., "Protein Sequence and Mass Spectrometric Analysis of Tau in the Alzheimer's Disease Brain," Journal of Biological Chemistry, 1992, vol. 267(24), pp. 17047-17054.

Hayashi et al., "Synthetic Hexa- and Heptapeptides That Inhibit IL-8 from Binding to and Activating Human Blood Neutrophils1," J. Immunol., 1995, vol. 154, pp. 814-824.

He et al., "Evidence for a Role of Platelet-Activating Factor (PAF) in the Pathogenesis of Age-Related Macular Degeneration (AMD)", Investigative Ophthalmology & Visual Science, 2007, vol. 48, Iss. 13, 2 pages. (Abstract only).

Hilton et al., "Food Contains the Bioactive Peptide, Cyclo(His-Pro)," J. Clin Endocrinol Metab, Aug. 1992, vol. 75(2), pp. 375-378 (Abstract Only Provided).

Hilton et al., "Identification and Characterization of Cyclo (His-Pro)-Like Immunoreactivity in Amniotic Fluid," Peptides, Mar.-Apr. 1989, vol. 10(2), pp. 299-301 (Abstract Only Provided).

Hilton et al., "Radioimmunoassay of Cyclo(His-Pro) in Unextracted Human Plasma: Report of a Normal Range and Definition of Factors Critical for Successful Assay," Neuropeptides, 1989, vol. 13(1), pp. 65-70 (Abstract Only Provided).

Hilton et al., "Relationship between Plasma Cyclo (His-Pro), a Neuropeptide Common to Processed Protein-Rich Food, C-Peptide/Insulin Molar Ratio in Obese Women," Nutr Neurosci, 2001, vol. 4(6), pp. 469-474 (Abstract Only Provided).

Hlinak et al., "Effect of alaptide, its analogues and oxiracetam on memory for an elevated plus-maze in mice," European Journal of Pharmacology, 1996, vol. 314, pp. 1-7.

Hoffman et al., "An Enzymatically Stable Peptide with activity in the Central Nervous System: Its Penetration through the Blood-CSF Barrier," Brain Res, Feb. 11, 1977, vol. 122(1), pp. 87-94 (Abstract Only Provided).

Holden et al., "Quorum-sensing cross talk: isolation and chemical characterization of cyclic dipeptides from *Pseudomonas aeruginosa* and other Gram-negative bacteria," Moleclur Microbiology, 1999, vol. 33(6), pp. 1254-1266.

Hollyfield et al., "Oxidative damage-induced inflammation initiates age-related macular degeneration," Nature Medicine, 2008, vol. 14, No. 2, pp. 194-198.

Hong et al., "Inhibitory effect against Akt of cyclic dipeptides isolated from *Bacillus* sp" J. Microbiol. Biotechnol., 18, 682-685 (2008).

Houston et al., "The cyclic dipeptide CI-4 [cyclo-(l-Arg-d-Pro)] inhibits family 18 chitinases by structural mimicry of a reaction intermediate," Biochem J., Nov. 15, 2002, vol. 368(Pt 1) (Abstract Only Provided).

Horwitz et al., "Piperazinedione plus total body irradiation: an alternative preparative regimen for allogeneic bone marrow transplantation in advanced phases of chronic myelogenous leukemia," Bone Marrow Transplantation, 1989, vol. 4, Iss. 1, pp. 101-105.

Hwang et al., "Effects of cyclo (his-pro) plus zinc on glucose metabolism in genetically diabetic obse mice," Diabetes Obes. Metab., Sep. 2003, vol. 5(5), pp. 317-324 (Abstract Only Provided).

Iriuchijima et al., "Thyrotripin-Releasing Hormone and Cyclo (His-Pro)-Like Immunoreactivities in the Cerebrospinal Fluids of 'Normal' Infants and Adults, and Patients with Various Neuropsychiatric and Neurologic Disorders," Life Sci. 1987, 41(22):2419-2428, Abstract only, from PubMed—PMID:2891013.

Ishibashi et al., "A Mechanism for Bitter Taste Sensibility in Peptides," Agric. Biol. Chem., 1988, vol. 52(3), pp. 819-827.

Ishibashi et al., "Bitterness of Leucine-Containing Peptides," Agric. Biol. Chem., 1987, vol. 51(9), pp. 2389-2394.

Ishii, et al. "Incidence of brain tumors in rats fed aspartame," Toxicology Letters, 1981, vol. 7, pp. 433-437.

Iyer et al. "Inflammatory lipid mediators in adipocyte function and obesity." Nature Reviews Endocrinology, Feb. 2010, vol. 6, pp. 71-82.

Jackson et al., "Amyotrophic Lateral Sclerosis: Thryrotropin-releasing hormone and histidyl proline diketopiperazine in the spinal cord and cerebrospinal fluid," Neurology, 1986, vol. 36(9), pp. 1218-1223.

Jamie et al., "The effect of the isomers of cyclo(Trp-Pro) on heart and ion-channel activity," J Pharm Pharmacol, Dec. 2002, vol. 54(12) (Abstract Only Provided).

Jara et al., "Elevated serum levels of cyclo (His-Pro), and endogenous inhibitor ofpituitary prolactin secretion, in systemic lupus erythematosus patients," Lupus, 1997, vol. 6(3) (Abstract Only Provided).

Jaspan et al., "Study of Passage of Peptides Across the Blood-Brain Barrier: Biological Effects of Cyclo(His-Pro) After Intravenous and Oral Administration," Annals of the New York Academy of Science, 1994, vol. 739, pp. 101-107 (Abstract Only Provided).

Jiang et al. "Asymmetric Reformastky reaction catalyzed by amino acid derivatives," Huaxue Tongbao CKNI, 2001, vol. 10, pp. 637-640 (English Abstract).

Jiang et al., "AKT signaling in regulating angiogenesis," Current Cancer Drug Targets, 2008, vol. 8, pp. 19-26.

Jicha et al., "Sequence Requirements for Formation of Conformational Variants of Tau Similar to Those Found in Alzheimer's Disease," Journal of Neuroscience Research, 1999, vol. 55, pp. 713-723.

Kaakkola et al., "Effects of two diketopiperazines, cyclo (His-Pro) and cyclo (Asp-Phe), on striatal dopamine: A microdialysis study," Brain Research Bulletin, 1993, vol. 32(6), pp. 667-672.

Kanzaki et al., "Enzymatic synthesis of dehydro cyclo(His-Phe)s, analogs of the potent cell cycle inhibitor, dehydrophenylahistin, and their inhibitory activities toward cell division," Biosci Biotechnol Biochem, Nov. 2004, vol. 68(11), pp. 2341-2345 (Abstract Only Provided).

Kasperska-Zajac et al. "Platelet Activating Factor as a Mediator and Therapeutic Approach in Bronchial Asthma." Inflammation, Apr. 2008, vol. 31, No. 2, pp. 112-120.

Kikwai et al, "Stability and degradation profiles of Spantide II in aqueous solutions," Eur J Pharm Sci, Feb. 2006, vol. 27(2-3), pp. 158-166, Epub Nov. 2, 2005. (Abstract Only Provided).

Kilian et al., "Biological activity of selected tyrosine-containing 2,5-diketopiperazines," Pharmazie, Apr. 2005, vol. 60(4), pp. 305-309 (Abstract Only Provided).

Kilian et al., "The effect of the isomer of cyclo(Trp-Pro) on heart and ion-channel activity," J. Pharm. Pharmacol., Dec. 2002, vol. 54(12), pp. 1659-1665 (Abstract Only Provided).

Kobayashi et al., "Neuropeptide Y and histidyl-proline diketopiperazine," Rinsho-Kensa, Japan, Sep. 1987, vol. 21, No. 9, pp. 984-991.

Kopple et al. "Conformation of Cyclo-(l-Threonine)2 and Cyclo-(l-Allo Threonine)2 : A Proton and Carbon N.m.r. Study." International Journal of Peptide Protein Research, Jul. 1981, vol. 18, No. 1, pp. 33-40.

Koskinen, "Effect of Low Intravenous Doses of TRH, Acid-TRH and Cyclo (His-Pro) on Cerebral and Peripheral Blood Flows," British Journal of Pharmacology, 1986, vol. 87(3), pp. 509-519 (Abstract Only Provided).

Kow et al., "The Effects of the TRH Metabolite Cyclo(His-Pro) and Its Analogs on Feeding," Pharmacology, Biochemistry & Behavior, 1991, vol. 38, pp. 359-364.

Kuenz et al., "Plasma levels of soluble adhesion molecules sPECAM-1, sP-selectin and sE-selectin are associated with relapsing-remitting disease course of multiple sclerosis," J. Neuroimmunol, Oct. 2005, vol. 167(1-2), pp. 143-149.

Kulikov et al., "Review: The Bioregulatory Role of Platelet-Activating Factor in Intracellular Processes and Cell-Cell Interactions," 1997, www.protein.bio.msu.su/biokhimiya/contents/v63/full/63010057.html, pp. 1-13.

Kullenberg et al., "Intraarticular Corticosteroid Injection: Pain Relief in Osteoarthritis of the Hip?," Journal of Rheumatology, 2004, vol. 31, No. 11, pp. 2265-2268.

Kurahashi et al., "Histydyl-Proline Diketopiperazine (HPD), A Metabolite of Thyrotropin-Releasing Hormone (TRH), Improves the Ataxic Gait in 3-Acetylpyridine (3-AP) Treated Rats," No To Shinkei, Sep. 1986, vol. 38(9), pp. 893-898 (Abstract Only Provided).

(56) References Cited

OTHER PUBLICATIONS

Larsen et al. "Kinetics of degradation and oil solubility of ester prodrugs of a model dipeptide (Gly-Phe)," Eur J Pharm Sci, Aug. 2004, vol. 22(5), pp. 399-408 (Abstract Only Provided).
Lechan et al., "Thyrotropin Releasing Hormone but not Histidyl-Proline Diketopiperazine is Depleted from Rat Spinal Cord Following 5,7-Dihydroxytryptamine Treatment," Brain Research, 1985, vol. 326(1), pp. 152-155 (Abstract Only Provided).
Lechin et al., "Plasma Neurotransmitters and Cortisol in Chronic Illness: Role of Stress," J Medicine, 1994, vol. 25(3-4), pp. 181-192 (Abstract Only Provided).
Leduque et al., "Histidyl-Proline Diketopiperazine (His-Pro DKP) Immunoreactivity is Present in the Glucagon-Containing Cells of the Human Fetal Pancreas," J Clin Invest, 1987, 79(3):875-880 (Abstract Only Provided).
Lee et al., "Characterization of an Elastase Inhibitor Produced by Streptomyces lavendulae SMF11," Journal of Microbiology and Biotechnology, 2000, vol. 10, No. 1, pp. 81-85.
Lee et al., "Cyclo (Leu-Gly attenuates the striatal dopaminergic supersensitivity induced by chronic morphine," Alcohol Drugs Res, 1987, vol. 7(1) (Abstract Only Provided).
Lehninger et al., "Amino Acids and Peptides," Chapter 5 of Principles of Biochemistry, 1993, 2nd edition, pp. 111-133.
Lewis et al., "Hydrogen Peroxide Stimulates the Synthesis of Platelet-activating Factor by Endothelium and Induces Endothelial Cell-dependent Neutrophil Adhesion," The Journal of Clinical Investigation, 1988, vol. 82, Iss. 6, pp. 2045-2055.
Lindsley et al., "Allosteric Akt (PKB) inhibitors: discovery and SAR of isozyme selective inhibitors," Bioorganic & Medicinal Chemistry Letters, 2005, vol. 15, Iss. 3, pp. 791-764.
Lindner et al., "[Effects of cyclic adenosine-3',5'-monophosphate and cyclo{Lys-Pro).HCl neuronotrophic factors in tissue culture]," J Hirnforsch, 1987, vol. 28(3) (Abstract Only Provided).
Liu et al., "Hydroxyprolylserine derivatives JBP923 and JBP485 exhibit the antihepatitis activities after gastrointestinal absorption in rats," J Pharmacol Exp Ther, Aug. 2000, vol. 294(2) (Abstract Only Provided).
Luca et al., "Determination of serotonin content and ceruloplasmin activity, of blood and CSF amino acid level in multiple sclerosis," Neurol Psychiatr (Bucur), 1986, vol. 24(3), pp. 153-159.
Lucietto et al., "The biological activity of the histidine-containing diketopiperazines cyclo (His-Ala) and cyclo (His-Gly)," Peptides, Nov. 2006, vol. 27(11), pp. 2706-2714, Epub Jun. 21, 2006 (Abstract Only Provided).
Lupia et al., "Role of tumor necrosis factor-α and platelet-activating factor in neoangiogenesis induced by synovial fluids of patients with rheumatoid arthritis," European Journal of Immunology, 1996, vol. 26, Iss. 8, pp. 1690-1694.
Ma et al., "Platelet-Activating Factor (PAF) Induces Corneal Neovascularization and Upregulates VEGF Expression in Endothelial Cells," Investigative Ophthalmology & Visual Science, 2004, vol. 45, No. 9, pp. 2915-2921.
Matejschuk et al., "Production of human albumin solution: a continually developing colloid," British Journal of Anaesthesia, 2000, vol. 85, Iss. 6, pp. 887-895.
Mayer, "Immunology—Chapter Four," Immunoglobulins—Structure and Function, online at pathmicro.med.sc.edu/mayer/IgStruct2000.htm, University of South Carolina School of Medicine, Nov. 6, 2009, 8 pages.
Mazza et al., "Potential energy calculations on phenylalanine rotamers in different boat forms of proline-containing cyclic dipeptides," Int. J. Pept. Protein Res., vol. 31, Feb. 1988, pp. 157-163.
McCain et al., "Endorphinergic modulation of immune function: potent action of the dipeptide glycyl-L-glutamine," Life Science, 1987, vol. 41, pp. 169-176.
McCain et al., "Modulation of Human T-Cell Suppressor Activity by Beta Endorphin and Glycyl-L-Glutamine," Int. J. Immunopharmoc, 1986, vol. 8(4), pp. 443-446.
McCleland et al., "An investigation into the biological activity of the selected histidine-containing diketopieperazines cyclo(His-Phe) and cyclo(His-Tyr)," Journal of Pharmacy and Pharmacology, Sep. 2004, vol. 56(9), pp. 1143-1153.
Meester et al., "In Vivo Inhibition of Dipeptidyl Peptidase IV Activity by Pro-Pro-diphenyl-phosphonate (Prodipine)," Biochemical Pharmacology, 1997, vol. 54, pp. 173-179.
Meltzer, "Efficacy and patient satisfaction with cromolyn sodium nasal solution in the treatment of seasonal allergic rhinitis: a placebo-controlled study," Clinical Therapeutics, 2002, vol. 24, Iss. 6, pp. 942-952.
Mentlein et al., "Dipeptidyl-Peptidase IV Hydrolyses Gastric Inhibitory Polypeptide, Glucagon-Like Peptide-1(7-36)amide, Peptide Histidine Methionine and is Responsible for their Degradation in Human Serum," European Journal of Biochemistry, 1993, vol. 214(3), pp. 829-835 (Abstract Only Provided).
Mesh, "Autoimmune Diseases," internet document www.ncbi.nlm.nih.gov/sites/entrez, accessed Oct. 31, 2007, 2 pages.
Michell et al., "Biomarkers and Parkinson's Disease," Brain, Aug. 2004, vol. 127, pp. 1693-1705.
Miller et al., "Peptide Inhibitor of Interleukin-8 (IL-8) Reduces Staphylococcal Enterotoxin-A (SEA) Induced Neutrophil Trafficking to the Lung," Inflamm. Res., 1996, vol. 45, pp. 393-397.
Milne, et al. "The biological activity of selected cyclic dipeptides," J. Pharm. Pharmacol., 1998, vol. 50, pp. 1331-1337.
Minelli et al., "Phosphoproteomic analysis of the effect of cyclo-[His-Pro] dipeptide on PC12 cells." Peptides, Jan. 2006;27(1):105-13. Epub Aug. 30, 2005., Abstract only PMID: 16137790.
Mitsuma et al., "Radioimmunoassay for Thyrotropin-Releasing Hormone Precursor Peptide, Lys-Arg-Gln-His-Pro-Gly-Arg-Arg," Exp Clin Endocrinology, 1989, vol. 93(1), pp. 53-60 (Abstract Only Provided).
Mizuma et al., "Concentration-Dependent Preferences of Absorptive and Excretive Transport Cause Atypical Intestinal Absorption of Cyclic Phenylalanylserine: Small Intestine Acts as an Interface Between the Body and Ingested Compounds," Research Communications in Molecular Pathology and Pharmacology, 2002, vol. 111, pp. 199-209.
Mizuma et al., "Intestinal Absorption of Stable Cyclic Glycylphenylalanine: Comparison with the Linear Form," J. Pharm. Pharmacol., 1997, vol. 49, pp. 1067-1071.
Molodavkin et al., "[Effect of the novel dipeptide nootropic agent noopept and its metabolite cyclo-L-prolylglycine on the transcallosal evoked potential in the rat brain]," Eksp Klin Farmakol, Mar.-Apr. 2002, vol. 65(2) (Abstract Only Provided).
Monaco et al., "Plasma and cerebrospinal fluid tryptophan in Multiple Sclerosis and Degenerative Diseases," J Neurol Neurosurg Psychiatry, 1979, vol. 42(7), pp. 640-641 (Abstract Only Provided).
Montine et al., "Cerebrospinal Fluid Ab42, Tau, and F2-Isoprostane Concentrations in Patients with Alzheimer Disease, Other Dementias, and in Age-Matched Controls," Acrch Pathol Lab. Med, Apr. 2001, vol. 125, pp. 510-512.
Mori et al., "Alteration by Liquid Protein Diet of TRH and Cyclo(His-Pro) in the Young Rat Brain," Res. Commun Chem Pathol Pharmacol, 1985, vol. 47(1), pp. 157-160 (Abstract Only Provided).
Mori et al., "Brain TRH and Cyclo (His-Pro) and Brain Protein in the Newborn Rat are Altered by Maternal Liquid Protein Feeding," Life Sci, 1983, vol. 32(14), pp. 1607-1612 (Abstract Only Provided).
Mori et al., "Distribution of histidyl-proline diketopiperazine [cyclo (His-Pro)] and thyrotropin-releasing hormone (TRH) in the primate central nervous system," Brain Res, 1982, vol. 245(1), pp. 183-186.
Mori et al., "Histidyl-Proline Diketopiperazine Cyclo (His-Pro): Identification and Characterization in Rat Pancreatic Islets," Biochem Biophys Res Commun, 1983, vol. 115(1), pp. 281-286 (Abstract Only Provided).
Mori et al., "Histidyl-Proline Diketopiperazine cyclo (His-Pro): measurement by radioimmunoassay in human blood in normal subject and in patients with hyper- and hypothyroidism," Biochem Biophys Res Commun, 1982, vol. 109(2), pp. 541-547.

(56) References Cited

OTHER PUBLICATIONS

Mori et al., "Regional Dissociation of Histidyl-Proline Diketopiperazine (Cyclo-(His-Pro)) and Thyrotropin-Releasing Hormone (TRH) in the Rat Brain," Brain Research, 1982, vol. 231(2), pp. 451-453 (Abstract Only Provided).
Mori et al., "Specific Radioimmunoassay of Cyclo (His-Pro), a Biologically Active Metabolite of Thyrotropin-Releasing Hormone," Endocrinology, 1981, vol. 108(5), pp. 1995-1997 (Abstract Only Provided).
Mori et al., ["TRH and Cyclo (His-Pro) Concentrations in the Young Rat Brain are Altered by a Liquid Protein Diet]," [Article in Japanese], Nippon Naibunpi Gakkai Zasshi, 1987, vol. 63(7), pp. 846-852 (English Abstract Only).
Morley et al., "Histidyl-proline diketopiperazine decreases food intake in rats," Brain Research, 1981, vol. 210, Iss. 1-2, pp. 475-478.
Morley et al., "Neuropeptides and appetite: contribution of neuropharmacological modeling," Fed. Proc., Nov. 1984, vol. 43(14), pp. 2903-2907 (Abstract Only Provided).
Moss et al. "Th1/Th2 cells in inflammatory disease states: therapeutic implications," Expert Opinion on Biological Therapy, Dec. 2004, vol. 4, No. 12, pp. 1887-1896.
Moss et al., "Kinetics and Mechanism of the Facile Cyclization of Histidyl-Prolineamide to Cyclo (His-Pro) in Aqueous Solution and the Competitive Influence of Human Plasma," J Pharm Pharmacol, 1990, vol. 42(1), pp. 7-12 (Abstract Only Provided).
Murray et al., "Role of α-Synuclein Carboxy-Terminus on Fibril Formation in Vitro," Biochemistry, 2003, vol. 42, pp. 8530-8540.
Nakamura et al., "T-cell mediated inflammatory pathway in osteoarthritis," Osteoarthritis & Cartilage, 1999, vol. 7, pp. 401-402.
Neustadt, "Intra-articular injections for osteoarthritis of the knee," Cleveland Clinic J. Med., 2006, vol. 73(10), pp. 897-911.
Nicholson et al., "NPI-2358 is a tubulin-depolymerizing agent: in-vitro evidence for activity as a tumor vascular-disrupting agent," Anticancer Drugs, Jan. 2006, vol. 17(1), pp. 25-31 (Abstract Only Provided).
Nicolson, "Metabolic syndrome and mitochondrial function: Molecular replacement and antioxidant supplements to prevent membrane peroxidation and restore mitochondrial function," Journal of Cellular Biochemistry, 2007, vol. 100, Iss. 6, pp. 1352-1369.
Nitecki et al., "A Simple Route to Sterically Pure Kiketopiperazines" J. Org. Chem., 1968, vol. 33(2), pp. 864-866.
O'Connor et al., "Post-proline dipeptidyl-aminopeptidase from synaptosomal membranes of guinea-pig brain," European Journal of Biochemistry, 1986, vol. 154, Iss. 2, pp. 329-335.
Ostrovskaia et al., "Multicomponent antithrombotic effect of the neuroprotective prolyl dipeptide GVS-111 and its major metabolite cyclo-L-prolylglycine," Eksp Klin Farmakol, Mar.-Apr. 2002, vol. 65(2) (Abstract Only Provided).
Otani et al., "Bone marrow-derived stem cells target retinal astrocytes and can promote or inhibit retinal angiogenesis," Nature Medicine, 2002, vol. 8, No. 9, pp. 1004-1010.
Oztuna et al., "Intra-articular Injection of Tenoxicam in Osteoarthritic Knee Joints With Effusion," Orthopedics, 2007, vol. 30, Iss. 12, pp. 1039-1042.
Palace et al. "Epilepsy: an autoimmune disease?" Journal of Neurology, Neurosurgery & Psychiatry, Dec. 2000, vol. 69, No. 6, pp. 711-714.
Palacios et al., "Tenidap Decreases IL-8 and Monocyte Chemotactic Peptide-1 (MCP-1) mRNA Expression in the Synovial Tissue of Rabbits with Antigen Arthritis and in Cultured Synovial Cells," Clin. Exp. Immunol., 1998, vol. 111, pp. 588-596.
Pandey et al., "Synthetic Peptides Corresponding to a Repetitive Sequence of Malarial Histidine Rich Protein Bind Haem and Inhibit Haemozoin Formation in vitro," Mol Biochem Parasitol, 1997, vol. 90(1), pp. 281-287 (Abstract Only Provided).
Parker et al., "Evidence for the Presence of Immunoreactive Histidyl-Proline Diketopiperazine [Cyclo (His-Pro)] in the Adult Human Brain," Peptides, Nov.-Dec. 1983, vol. 4(6), pp. 879-881 (Abstract Only Provided).
Pötgens et al., "Covalent dimerization of vascular permeability factor/vascular endothelial growth factor is essential for its biological activity. Evidence from Cys to Ser mutations," The Journal of Biological Chemistry, 1994, vol. 269, Iss. 52, pp. 32879-32885.
Pekary et al., "In vitro Production of a TRH-Homologous Peptide and His-Pro Diketopiperazine by Human Semen," J Androl, 1985, vol. 6(6), pp. 379-385 (Abstract Only Provided).
Potocka et al., "Pharmacokinetic characterization of the novel pulmonary delivery excipient fumaryl diketopiperazine," J. Diabetes Sci. Technol., Sep. 2010, vol. 4(5), pp. 1164-1173 (Abstract Only Provided).
Prakash et al., "Synthesis and Biological Activity of Novel Neuroprotective Diketopiperazines," Bioorganic & Medicinal Chemistry, Sep. 2002, vol. 10(9), pp. 3043-3048.
Prasad et al., "Distribution and Characterization of Cyclo (His-Pro)-Like Immunoreactivity in Human Cerebrospinal Fluid," Biochem Biophys Res Commun, 1986, vol. 136(2), pp. 835-842 (Abstract Only Provided).
Prasad et al., "Distribution and Metabolism of Cyclo (His-Pro): A New Member of the Neuropeptide Family," Peptides, May-Jun. 1982, vol. 3(3), pp. 591-598 (Abstract Only Provided).
Prasad et al., "Increased cerebrospinal fluid cyclo(His-Pro) content in schizophrenia," Neuropeptides, Nov. 1991, vol. 20(3), pp. 187-190.
Prasad et al., "Isolation of cyclo(His-Pro)-like immunoreactivity from Human Urine and Demonstration of its Immunologic, Pharmacologic, and Physico-chemical Identity with the Synthetic Peptide," Biochemistry Int, 1990, vol. 21(3), pp. 425-434 (Abstract Only Provided).
Prasad et al., "Thermoregulation in rats: opposing effects of thyrotropin releasing hormone and its metabolite histidyl-proline diketopiperazine," Biochem Biophys Res. Commun., 1978, vol. 85(4), pp. 1582-187.
Prasad, "Bioactive Cyclic Dipeptides," Peptides, 1995, vol. 16(1), pp. 151-164.
Purves et al. (Eds), Neuroscience, 2001, Sinauer Associates, Inc., 2nd Edition, pp. 75, 367, 400 and 403.
Purves et al., Life: the Science of Biology, 3rd Ed. (1992), p. 376.
Rainbow et al., "Distribution, survival and biological effects in mice of a behaviorally active, enzymatically stable peptide: pharmacokinetics of cyclo(Leu-Gly) and puromycin-induced amnesia," Pharmacol Biochem Behav, May 1979, vol. 10(5), pp. 787-793.
Rainger et al., "Endothelial-Borne Platelet-Activating Factor and Interleukin-8 Rapidly Immobilize Rolling Neutrophils," Am. J. Physiol., 272(Heart Circ. Physiol. 41):H114-H122 (1997).
Rainsford et al., "Effects of 5-Lipoxygenase Inhibitors on Interleukin Production by Human Synovial Tissues in Organ Culture: Comparison with Interleukin-1-Synthesis Inhibitors," J. Pharm. Pharmacol., 48:46-52 (1996).
Ramírez et al., "Platelet Activating Factor Modulates Microvascular Permeability through Nitric Oxide Synthesis," Microvascular Research, 1995, vol. 50, Iss. 2, pp. 223-234.
Reubsaet et al., "Qualitative and Quantitative Aspects of the Degradation of Several Tripeptides Derived from the Antitumor Peptide Antagonist [Arg(6), D-Trp(7,9), MePhe(8)] Substance P[6-11]," J Pharm Biomed Anal 1999, 19(3-4):2.
Rinaldi et al. "Immunological markers in multiple sclerosis: tackling the missing elements," Neurol. Sci., Dec. 2005, vol. 26 Suppl. 4, pp. S215-S217.
Rosenthal et al., "Effects of Arachidonic Acid and Cyclo (His-Pro) on Zinc Transport Across Small Intestine and Muscle Tissues," Life Sci, 2001, vol. 70(3), pp. 337-348 (Abstract Only Provided).
Roth et al., "Platelet-Activating Factor Exerts Mitogenic Activity and Stimulates Expression of Interleukin 6 and Interleukin 8 in Human Lung Fibroblasts via Binding to its Functional Receptor," J. Exp. Med., 1996, vol. 184, pp. 191-201.
Sakkas et al., "T Cells and T-Cell Cytokine Transcripts in the Synovial Membrane in Patients with Osteoarthritis", Clinical and Diagnostic Laboratory Immunology, Jul. 1998, vol. 5, No. 4, pp. 430-437.
Sakurada et al., "Antinociceptive activities of synthetic dipeptides in mice." J. Pharm. Pharmacol., 1982, vol. 34, pp. 750-751.
Sakuta et al., "Dual Regulatory Effects of Interferon-α, -β, and -γ on Interleukin-8 Gene Expression by Human Gingival Fibroblasts in

(56) References Cited

OTHER PUBLICATIONS

Culture Upon Stimulation with Lipopolysaccharide from Prevotella Intermedia, Interleukin-1α, or Tumor Necrosis Factor-α," J. Dent Res., 1998, vol. 77(8), pp. 1597-1605.
Samanta et al., "Crystal Structure of Human Plasma Platelet-activating Factor Acetylhydrolase," J. Biol. Chem., vol. 283(46), Nov. 14, 2008, pp. 31617-31624.
Sammes, "Naturally Occurring 2,5-Dioxopiperazines and Related Compounds," Fortschr. Chem. Org. Naturst., 1975, vol. 32, pp. 51-118.
Sano et al. "Process Research and Development of L-Alanyl-L-Glutamine, a Component of Parenteral Nutrition," Organic Process Research & Development, 2000, vol. 4, pp. 147-152.
Sato et al., "Comparison of the antiociceptive effect between the cyclic dipeptide cyclo[Tyr(Et)-homoarginine] and the linear dipeptide Boc-Tyr(Et)-homoarginine-Ome in rats.," Jpn J Pharmacol, Jan. 1984, vol. 34(1) (Abstract Only Provided).
Scharpe et al., "Peptide Truncation by Dipeptidyl Peptidase IV: A New Pathway for Drug Discovery," Verh K. Acad Geneeskd Belg. 2001, vol. 63(1), pp. 5-32 (Abstract Only Provided).
Schlingemann et al., "Role of vascular permeability factor/vascular endothelial growth factor in eye disease," Brit. J. Ophthalmology, vol. 81, 1997, pp. 501-512.
Sepetov et al., "Rearrangement, Racemization and Decomposition of Peptides in Aqueous Solution," Peptide Research, 1991, vol. 4(5), pp. 308-313 (Abstract Only Provided).
Seredenin et al. "Endogenous dipeptide cycloprolylglycine shows selective anxiolytic activity in animals with manifest fear reaction," Bull Exp Biol Med; Apr. 2002; vol. 1333(4) (Abstract Only Provided).
Shaw et al., "Future of early detection of lung cancer: the role of mouse models." Clin Cancer Res., Jul. 1; 11(13 Pt 2): 4999s-5003s, 2005.
Shimazaki et al., "Diketopiperazine Derivatives, a New Series of Platelet-Activating Factor Inhibitors," Chem. Pharm. Bull., 1987, vol. 35(8), pp. 3527-3530.
Shimazaki et al., "Diketopiperazines as a New Class of Platelet-Activating Factor Inhibitors," J. Med. Chem., 1987, vol. 30, pp. 1706-1709.
Shimazaki et al., "PAF Inhibitory Activity of Diketopiperazines: Structure-Activity Relationships," Lipids, 1991, vol. 26(12), pp. 1175-1178.
Shimi et al., "Isolation of Cairomycins A and C," Antimicrobial Agents and Chemotherapy, Jun. 1981, vol. 19(6), pp. 941-944.
Shimonkevitz et al., "A Diketopiperazine Fragment of Human Serum Albumin Modulates T-Lymphocyte Cytokine Production Through Rap1," Journal of Trauma, Injury, Infection, and Critical Care, 2008, vol. 64, No. 1, pp. 35-41.
Shukla et al., "Role of Endogenous Cyclo(His-Pro) in Cold-Induced Hypothermia in the Desert Rat (*Mastomys natalensis*)," Peptides; 1994; 15(8):1471-4 (Abstract Only Provided).
Shutov et al., "[Diagnostic Significance of the type of In Vitro Interaction between Blood Lymphocytes and Serotonin in Multiple Sclerosis]," [Article in Russian], Zh Nevrol Psikhiatr Im S S Korsakova, 2002, vol. 102(4), pp. 35-38 (Abstract Only Provided).
Skates et al., "Molecular markers for early detection of renal carcinoma: investigative approach," Clin Cancer Res, Sep. 2004, vol. 10(18 Pt 2), pp. 6296S-6301S.
Slater, "Gas-liquid chromatography of 2,5-diketopiperazines as their trifluoroacetyl derivatives," Journal of Chromatography A, 1972, vol. 64, Iss. 1, pp. 166-169.
Smith et al., "Lesson 10, vol. 12—Asthma: Evolving Anti-Inflammatory Therapy," www.chestnet.org/education/pccu/vol12/lesson10.html, pp. 1-8, printed Jul. 20, 2000.
Smith et al., "Recent developments in drug therapy for multiple sclerosis," Mult. Scler., 1999, vol. 5, pp. 110-120.
Smith et al., "Solid-phase synthesis of a library of piperazinediones and diazepinediones via Kaiser oxime resin." Bioorg. Med. Chem., 1998, vol. 8, pp. 2369-2374.
Sollid et al. "Is celiac disease an autoimmune disorder?" Current Opinion in Immunology, Dec. 2005, vol. 17, No. 6, pp. 595-600.
Sollis "Short and novel stereospecific synthesis of trisubstituted 2,5-diketopiperazines," J Org Chem, Jun. 2005, vol. 70(12), pp. 4735-4740 (Abstract Only Provided).
Song et al., "Body weight reduction in rats by oral treatment with zinc plus cyclo-(His-Pro)," Br. J. Pharmacol., Sep. 2009, vol. 158(2), pp. 442-450, Epub May 5, 2009 (Abstract Only Provided).
Song et al., "Raw vegetable food containing high cyclo (his-pro) improved insulin sensitivity and body weight control," Metabolism, Nov. 2005, vol. 54(11), pp. 1480-1489 (Abstract Only Provided).
Song et al., "Synergistic Antidiabetic Activities of Zinc, Cyclo (His-Pro), and Arachidonic Acid," Metabolism 2001 50(1):53-59 (Abstract Only Provided).
Stark et al., "Structures, sensory activity, and dose/response functions of 2,5-diketopiperazines in roasted cocoa nibs (*Theobroma cacao*)." J Agric Food Chem., Sep. 7, 2005, vol. 53(18), pp. 7222-7231 (Abstract Only Provided) PMID: 16131134.
Steiner et al., "Histidyl Proline Diketopiperazine (Cyclo [His-Pro]) in Eating Disorders," Neuropeptides, Oct. 1989, vol. 14(3), pp. 185-189 (Abstract Only Provided).
Strom et al., "Lactobacillus plantarum MiLAB 393 produces the antifungal cyclic dipeptides cyclo(L-Phe-L-Pro) and cyclo(L-Phe-trans-4-OH-L-Pro) and 3-phenyllactic acid.," Appl Environ Microbiol, Sep. 2002, vol. 68(9) (Abstract Only Provided).
Suguna et al., "Crystal structures of diketopiperazines containing α-aminoisobutyric acid: Cyclo(Aib-Aib) and cyclo(Aib-L-Ile)," Biopolymers, 1982, vol. 21, Iss. 9, pp. 1847-1855.
Suzuki et al., "Effect of cyclic dipeptides containing histidine on pentobarbital narcosis," J. Pharm. Dyn., May 1981, vol. 4(5), pp. 377-379.
T Hart et al., "Evaluating the validity of animal models for research into therapies for immune-based disorders," DDT, 2004, vol. 9(12), pp. 517-524.
Takahara et al., "Detection in Human Serum by Radioimmunoassay of Histidyl-Proline Diketopiperazine, a Metabolite of Thyrotropin-Releasing Hormone," J Clinical Endocrinology, 1983, vol. 56(2), pp. 312-319 (Abstract Only Provided).
Tascioglu et al., "Efficacy of intra-articular sodium hyaluronate in the treatment of knee osteoarthritis," Clinical Rheumatology, 2003, vol. 22, Iss. 2, pp. 112-117.
Teitel et al., "Rheumatoid arthritis," PubMed Health, reviewed Feb. 2, 2012, available at www.ncbi.nlm.nih.gov/pubmedhealth/PMH0001467/?report=printable, 8 pages.
Teitel et al., "Scleroderma," PubMed Health, reviewed Feb. 2, 2012, available at www.ncbi.nlm.nih.gov/pubmedhealth/PMH0001465/?report=printable, 7 pages.
Teitel et al., "Systemic lupus erythematosus," PubMed Health, reviewed Feb. 2, 2012, available at www.ncbi.nlm.nih.gov/pubmedhealth/PMH0001471/?report=printable, 9 pages.
Unal et al., "Cyclo(Gly-Gln) inhibits the cardiorespiratory depression produced by beta-endorphin and morphine," Brain Research, 1997, vol. 747(1), pp. 52-59.
Vara et al., "PI3K/Akt signalling pathway and cancer," Cancer Treatment Reviews, 2004, vol. 30, pp. 193-204.
Varughese et al., "Crystal structure and conformation of cyclo-L-cystine," Int. J. Pept. Protein Res., vol. 18, Jul. 1981, pp. 88-102.
Vogel et al., "Disseminated tumor cells—Their detection and significance for prognosis of gastrointestinal and pancreatic carcinomas," Virchows Arch, 2001, vol. 439, pp. 109-117.
Walter et al., "Neurohypophyseal hormones, analogs, and fragments: their effect on puromycin-induced amnesia," Proc. Natl. Acad. Sci., Oct. 1975, vol. 72(10), pp. 4180-4184.
Walter et al., "The Cyclized C-Terminal Dipeptide of Arginine Vasopressin: Metabolic Stability and Antagonism of Puromycin-Induced Amnesia," Hormones and Behavior, 1982, vol. 16; p. 234-244.
Wang et al., "A facile pathway to synthesize diketopiperazine derivatives," Tetrahedron Lett, 2002, vol. 43, pp. 865-867.
Wang et al., "Novel inhibitors of plasminogen activator inhibitor-1: development of new templates from diketopiperazines," Bioorg Med Chem Lett, Sep. 2002, vol. 12(17), pp. 2367-2370 (Abstract Only Provided).

(56) References Cited

OTHER PUBLICATIONS

Watterson et al., "Viscosupplementation: Therapeutic Mechanisms and Clinical Potential in Osteoarthritis of the Knee," Journal of the American Academy of Orthopaedic Surgeons, 2000, vol. 8, No. 5, pp. 277-284. Abstract Only.

Weng et al., "Novel CCK-B receptor agonists: diketopiperazine analogues derived for CCK4 bioactive conformation," Regul Pept, Aug. 1996; vol. 65(1) (Abstract Only Provided).

Wennemers et al., "Diketopiperazine Receptors: A Novel Class of Highly Selective Receptors for Binding Small Peptides," Chem. Eur. J., 2001, vol. 7, No. 15, pp. 3342-3347.

Wilber et al., "Endogenous histidyl-proline diketopiperazine [cyclo (His-Pro)]: a potential satiety neuropeptide in normal and genetically obese rodents," Trans Assoc Am Physicians, 1983, vol. 96, pp. 131-136.

Wilber et al., "Histidyl-proline diketopiperazine: a potent and chronic appetite-inhibiting neuropeptide," Trans Assoc. Am Physicians, 1986, vol. 99, pp. 245-249.

Wilkes et al. "Patient Survival after Human Albumin Administration: A Meta-Analysis of Randomized, Controlled Trials." Annals of Internal Medicine, Aug. 2001, vol. 135, No. 3, pp. 149-164.

Wisniewski et al., "Relationship between serum cyclo (His-Pro) concentrations and the nutritional status of HIV-infected patients," South Med. J., Mar. 1994, vol. 87(3), pp. 348-351 (Abstract Only Provided).

Woehlecke et al., "Reversal of breast cancer resistance protein-mediated drug resistance by tryprostatin A.," Int J Cancer; Dec. 2003, vol. 107(5) (Abstract Only Provided).

Wolf et al., "Identification of Cyclo(His-Pro)-Like Immunoreactivity in Human Follicular Fluid: Correlation with Steroid and Peptide Hormones," J Soc Gynecol Investigation, 1994, vol. 1(3), pp. 220-224 (Abstract Only Provided).

Wretlind, "The Availability of the Isopropyl Ester of L- and D-Phenylalanine and 3,6-Dibenzyl-2,5-Diketopiperazine form Growth in Rats," Acta phys. Scandinav, May 1953, vol. 30, pp. 97-104.

Wyatt et al., "2,5-Diketopiperazines as potent and selective oxytocin antagonists 1: Identification, stereochemistry and initial SAR," Bioorg Med Chem Lett., May 16, 2005, vol. 15(10), pp. 2579-2582 (Abstract Only Provided) PMID: 15863320.

Yamada et al., "Abundance of Cyclo (His-Pro)-like Immunoreactivity in the Brain of TRH-Deficient Mice," Endocrinology, Jan. 1999, vol. 140(1), pp. 538-541 (Abstract Only Provided).

Yanagisawa et al., "The Subcellular and Organ Distribution and Natural Form of Histidyl-Proline Diketopiperazine in Rat Brain Determined by a Specific Radioimmunoassay," J Biol Chem, Nov. 10, 1980, vol. 255(21), pp. 10290-10294 (Abstract Only Provided).

Yang et al., "Increased hepatic platelet activating factor (PAF) and PAF receptors in carbon tetrachloride induced liver cirrhosis." Gut, Jan. 2004, vol. 53, No. 6, pp. 877-883.

Yasukawa, "Inflammation in age-related macular degeneration: pathological or physiological?", Expert Review of Ophthalmology, 2009, vol. 4, Iss. 2, pp. 107-112.

Yi ES, "Hypersensitivity pneumonitis," Crit Rev Clin Lab Sci., Nov. 2002, vol. 39(6), pp. 581-629.

Yoshida et al., "PAF Inhibitors of Microbial Origin," Prog. Biochem. Pharmacol., 1988, vol. 22, pp. 68-80.

Youngblood et al., "Bovine Serum Albumin-GABA-His-Pro-NH2: an Immunogen for Production of Higher Affinity Antisera for TRH," J Neursci Methods, 1983, vol. 9(4), pp. 367-373 (Abstract Only Provided).

Zander et al., "Allogeneic bone marrow transplantation for acute leukemia refractory to induction chemotherapy," Cancer, 1985, vol. 56, Iss. 6, pp. 1374-1379.

Zeng et al., "Synthesis of a small library of diketopiperazines as potential inhibitors of calpain," Bioorg Med Chem Lett, Jun. 2005, vol. 15(12), pp. 3034-3038.

Zieve, "Multiple sclerosis," PubMed Health, reviewed Sep. 26, 2011, available at www.ncbi.nlm.nih.gov/pubmedhealth/PMH0001747/?report=printable, 10 pages.

Ziong et al., "Chemical Constituents from Phytolacca polyandra" Yunnan Zhiwu Yanjiu, 2002, vol. 24, No. 3, pp. 401-405. (English abstract).

International Search Report and Written Opinion for International (PCT) Patent Application No. PCT/US12/59483, dated Dec. 28, 2012 9 pages.

International Preliminary Report on Patentability for International (PCT) Patent Application No. PCT/US12/59483 dated Apr. 24, 2014, 7 pages.

Official Action for Australian Patent Application No. 2012323320 dated May 19, 2016, 3 pages.

Notice of Acceptance for Australian Patent Application No. 2012323320 dated May 1, 2017, 1 page.

Official Action (English translation) for Chinese Patent Application No. 201280047650.0 dated Mar. 24, 2015, 7 pages.

Official Action (English translation) for Chinese Patent Application No. 201280047650.0 dated Nov. 18, 2015, 5 pages.

Official Action (English translation) for Chinese Patent Application No. 201280047650.0 dated Jun. 21, 2016, 6 pages.

Official Action (with English translation) for Eurasian Patent Application No. 201490736/28 dated Jul. 29, 2015, 4 pages.

Official Action (with English translation) for Eurasian Patent Application No. 201490736/28 dated Mar. 25, 2016, 2 pages.

Notice of Allowance (with English translation) for Eurasian Patent Application No. 201490736/28 dated Oct. 18, 2016, 4 pages.

Extended European Search Report for European Patent Application No. 12840601.4 dated Dec. 22, 2014, 6 pages.

Official Action for European Patent Application No. 12840601.4 dated May 31, 2017, 5 pages.

Official Action for European Patent Application No. 12840601.4 dated Oct. 30, 2018, 4 pages.

Summons to Attend Oral Proceedings for European Patent Application No. 12840601.4 dated Aug. 5, 2019, 10 pages.

Official Action (with English translation) for Indonesian Patent Application No. P00201402452 dated May 24, 2018, 3 pages.

Official Action (with English translation) for Israeli Patent Application No. 231120 dated Feb. 7, 2017, 6 pages.

Official Action (with English translation) for Israeli Patent Application No. 231120 dated Nov. 1, 2017, 8 pages.

Official Action (with English translation) for Japanese Patent Application No. 2014-534833 dated Jul. 19, 2016, 4 pages.

Official Action (with English translation) for Japanese Patent Application No. 2014-534833 dated Mar. 14, 2017, 5 pages.

Official Action (with English translation) for Japanese Patent Application No. 2014-534833 dated Aug. 22, 2017, English translation, 7 pages.

Official Action for New Zealand Patent Application No. 623871 dated Feb. 9, 2015, 2 pages.

Official Action for Malaysian Patent Application No. PI 2014700476 dated Oct. 15, 2018, 3 pages.

Notice of Acceptance for New Zealand Patent Application No. 623871 dated Feb. 12, 2016, 1 page.

Official Action for Philippines Patent Application No. 1/2014/500686 dated Dec. 4, 2017, 5 pages.

Official Action for U.S. Appl. No. 14/350,617 dated Apr. 17, 2015, 9 pages.

Official Action for U.S. Appl. No. 14/350,617 dated Jan. 11, 2016, 12 pages.

Official Action for U.S. Appl. No. 14/350,617 dated Jul. 12, 2016, 12 pages.

Official Action for U.S. Appl. No. 14/350,617 dated Mar. 8, 2017, 11 pages.

Notice of Allowance for U.S. Appl. No. 14/350,617 dated Dec. 18, 2017, 8 pages.

Official Action for U.S. Appl. No. 15/896,964 dated Nov. 1, 2018, 11 pages.

Official Action for U.S. Appl. No. 15/896,964 dated Mar. 15, 2019, 9 pages.

Notice of Allowance for U.S. Appl. No. 15/896,964 dated Jun. 20, 2019, 9 pages.

Millett et al., "Shoulder Osteoarthritis: Diagnosis and Management", American Family Physician, 2008, vol. 78, Iss. 5, pp. 605-611.

IMPLANTABLE MEDICAL DEVICES WITH INCREASED IMMUNE TOLERANCE, AND METHODS FOR MAKING AND IMPLANTING

CROSS REFERENCE TO RELATED APPLICATIONS

This application is a continuation of U.S. patent application Ser. No. 15/896,964, filed Feb. 14, 2018, now U.S. Pat. No. 10,471,178, which is a continuation of U.S. patent application Ser. No. 14/350,617, filed on Apr. 9, 2014, now U.S. Pat. No. 9,925,300, which is a national stage application under 35 U.S.C. 371 of PCT Application No. PCT/US2012/059483, having an international filing date of Oct. 10, 2012, which designated the United States, which claims the benefit of priority under 35 U.S.C. § 119(e) to U.S. Provisional Patent Application No. 61/545,465, filed Oct. 10, 2011. The entire disclosure of U.S. Provisional Patent Application No. 61/545,465, U.S. patent application Ser. No. 14/350,617, and U.S. patent application Ser. No. 15/896,964 are incorporated herein by reference in their entirety.

FIELD OF INVENTION

The present invention relates to the contacting one or more surfaces of an implantable medical device with one or more diketopiperazines (DKPs).

BACKGROUND OF THE INVENTION

Implantation of a medical device into a patient's body can trigger an abnormal immune response by the patient's body which is a threat to the acceptance of the implant and can result in device failure. For the patient, this can mean extended inflammation, higher risk of infection, and tissue build-up that may cause complications as well as discomfort. These effects slow patient recovery and often mean further medical intervention.

SUMMARY OF THE INVENTION

The present invention provides for a method to prepare an implantable medical device for implantation in a subject comprising contacting the device with a DKP.

The invention further provides for a method for implanting a medical device comprising implanting a medical device into a subject, wherein a surface of the device comprises a DKP.

In one aspect, the methods comprise a DKP comprising the following formula

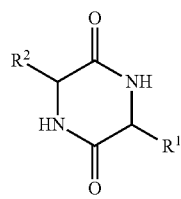

wherein:
$R^1$ and $R^2$, which may be the same or different, each is:
(a) a side chain of an amino acid, wherein the amino acid is glycine, alanine, valine, norvaline, α-aminoisobutyric acid, 2,4-diaminobutyric acid, 2,3-diaminobutyric acid, leucine, isoleucine, norleucine, serine, homoserine, threonine, aspartic acid, asparagine, glutamic acid, glutamine, lysine, hydroxylysine, histidine, arginine, homoarginine, citrulline, phenylalanine, p-aminophenylalanine, tyrosine, tryptophan, thyroxine, cysteine, homocysteine, methionine, penicillamine or ornithine; provided, however, that when $R^1$ is the side chain of asparagine or glutamine, then $R^2$ cannot be the side chain of lysine or ornithine, and when $R^1$ is the side chain of lysine or ornithine, then $R^2$ cannot be the side chain of asparagine or glutamine;
(b) $R^1$ is —$CH_2$—$CH_2$—$CH_2$— or —$CH_2$—CH(OH)—$CH_2$— and together with the adjacent ring nitrogen forms proline or hydroxyproline, $R^2$ is —$CH_2$—$CH_2$—$CH_2$— or —$CH_2$—CH(OH)—$CH_2$— and together with the adjacent ring nitrogen forms proline or hydroxyproline, or both $R^1$ and $R^2$ are each independently —$CH_2$—$CH_2$—$CH_2$— or —$CH_2$—CH(OH)—$CH_2$— and together with the adjacent ring nitrogens form proline or hydroxyproline; or
(c) a derivative of a side chain of an amino acid, wherein the amino acid is one of those recited in (a), and the derivatized side chain has:
  (i) an —$NH_2$ group replaced by an —$NHR^3$ or —$N(R^3)_2$ group, wherein each $R^3$ may independently be a substituted or unsubstituted alkyl, cycloalkyl, heterocycloalkyl, aryl, alkylaryl, arylalkyl or heteroaryl;
  (ii) an —OH group replaced by an —O—$PO_3H_2$ or —$OR^3$ group, wherein each $R^3$ may independently be a substituted or unsubstituted alkyl, cycloalkyl, heterocycloalkyl, aryl, alkylaryl, arylalkyl or heteroaryl;
  (iii) a —COOH group replaced by a —$COOR^3$ group, wherein each $R^3$ may independently be a substituted or unsubstituted alkyl, cycloalkyl, heterocycloalkyl, aryl, alkylaryl, arylalkyl or heteroaryl;
  (iv) a —COOH group replaced by a —$CON(R^4)_2$ group, wherein each $R^4$ may independently be H or a substituted or unsubstituted alkyl, cycloalkyl, heterocycloalkyl, aryl, alkylaryl, arylalkyl or heteroaryl;
  (v) an —SH group replaced by —S—S—$CH_2$—CH($NH_2$)—COOH or —S—S—$CH_2$—$CH_2$—CH($NH_2$)—COOH;
  (vi) a —$CH_2$— group replaced by a —CH($NH_2$)— or a —CH(OH)— group;
  (vii) a —$CH_3$ group replaced by a —$CH_2$—$NH_2$ or a —$CH_2$—OH group; and/or
  (viii) an H which is attached to a carbon atom replaced by a halogen; or a physiologically-acceptable salt thereof.

The implantable medical device can be selected from a graft, catheter, stent, prosthetic, breast implant, pump, tube, pin, rod, screw, brace, plate and pace maker. In one aspect, the stent can be selected from a cardiac stent, an artery stent and a birth control stent. In another aspect, the prosthetic can be selected from an artificial hip, an artificial knee and an artificial ankle. In still another aspect, the pump can be an insulin pump. In yet another aspect, the implantable medical device is composed of material selected from metal, steal, titanium, glass, polymers, plastics and ceramics.

In one aspect, the DKP is adhered to the surface of the implantable medical device. In another aspect, the DKP is impregnated into the surface of the implantable medical device. In still another aspect, the DKP is coated onto the surface of the implantable medical device. In yet another aspect, the implantable medical device is contacted with a solution comprising a DKP, wherein the solution adheres to the device.

In some embodiments, the DKP that adheres to the surface of the implantable medical device, or is impregnated into the surface of the implantable medical device or coated onto the surface of the implantable medical device, can be in an amount of about 1 μM to about 500 μM. In still another aspect, the amount can be in an amount of about 50 μM to about 100 μM.

In some embodiments, the concentration of the DKP on a surface of the implantable medical device exposed to the body is about 1 ng/cm$^2$ to about 200 ng/cm$^2$. In another aspect, the concentration of the DKP on a surface of the implantable medical device exposed to the body is about 50 ng/cm$^2$.

The subject of the methods can be a mammal, including a human.

In some embodiments, the subject's immune tolerance to the device is increased by the presence of the DKP.

Another embodiment of the invention relates to an implantable medical device, wherein a surface of the device comprises a DKP. In one aspect, the device comprises a DKP comprising the following formula

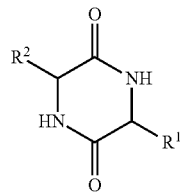

wherein:
R$^1$ and R$^2$, which may be the same or different, each is:
(a) a side chain of an amino acid, wherein the amino acid is glycine, alanine, valine, norvaline, α-aminoisobutyric acid, 2,4-diaminobutyric acid, 2,3-diaminobutyric acid, leucine, isoleucine, norleucine, serine, homoserine, threonine, aspartic acid, asparagine, glutamic acid, glutamine, lysine, hydroxylysine, histidine, arginine, homoarginine, citrulline, phenylalanine, p-aminophenylalanine, tyrosine, tryptophan, thyroxine, cysteine, homocysteine, methionine, penicillamine or ornithine; provided, however, that when R$^1$ is the side chain of asparagine or glutamine, then R$^2$ cannot be the side chain of lysine or ornithine, and when R$^1$ is the side chain of lysine or ornithine, then R$^2$ cannot be the side chain of asparagine or glutamine;
(b) R' is —CH$_2$—CH$_2$—CH$_2$— or —CH$_2$—CH(OH)—CH$_2$— and together with the adjacent ring nitrogen forms proline or hydroxyproline, R$^2$ is —CH$_2$—CH$_2$—CH$_2$— or —CH$_2$—CH(OH)—CH$_2$— and together with the adjacent ring nitrogen forms proline or hydroxyproline, or both R$^1$ and R$^2$ are each independently —CH$_2$—CH$_2$—CH$_2$— or —CH$_2$—CH(OH)—CH$_2$— and together with the adjacent ring nitrogens form proline or hydroxyproline; or
(c) a derivative of a side chain of an amino acid, wherein the amino acid is one of those recited in (a), and the derivatized side chain has:
(i) an —NH$_2$ group replaced by an —NHR$^3$ or —N(R$^3$)$_2$ group, wherein each R$^3$ may independently be a substituted or unsubstituted alkyl, cycloalkyl, heterocycloalkyl, aryl, alkylaryl, arylalkyl or heteroaryl;
(ii) an —OH group replaced by an —O—PO$_3$H$_2$ or —OR$^3$ group, wherein each R$^3$ may independently be a substituted or unsubstituted alkyl, cycloalkyl, heterocycloalkyl, aryl, alkylaryl, arylalkyl or heteroaryl;
(iii) a —COOH group replaced by a —COOR$^3$ group, wherein each R$^3$ may independently be a substituted or unsubstituted alkyl, cycloalkyl, heterocycloalkyl, aryl, alkylaryl, arylalkyl or heteroaryl;
(iv) a —COOH group replaced by a —CON(R$^4$)$_2$ group, wherein each R$^4$ may independently be H or a substituted or unsubstituted alkyl, cycloalkyl, heterocycloalkyl, aryl, alkylaryl, arylalkyl or heteroaryl;
(v) an —SH group replaced by —S—S—CH$_2$—CH(NH$_2$)—COOH or —S—S—CH$_2$—CH$_2$—CH(NH$_2$)—COOH;
(vi) a —CH$_2$— group replaced by a —CH(NH$_2$)— or a —CH(OH)— group;
(vii) a —CH$_3$ group replaced by a —CH$_2$—NH$_2$ or a —CH$_2$—OH group; and/or
(viii) an H which is attached to a carbon atom replaced by a halogen; or a physiologically-acceptable salt thereof.

The device can be selected from a graft, catheter, stent, prosthetic, breast implant, pump, tube, pin, rod, screw, brace, plate and pace maker. In yet another aspect, the device is composed of material selected from metal, steal, titanium, glass, polymers, plastics and ceramics.

In one aspect, the DKP is adhered to the surface of the device. In another aspect, the DKP is impregnated into the surface of the device. In still another aspect, the DKP is coated onto the surface of the device. In yet another aspect, the device is contacted with a solution comprising a DKP, wherein the solution adheres to the device.

In some embodiments, the DKP that adheres to the surface of the device, or is impregnated into the surface of the device or coated onto the surface of the device, can be in an amount of about 1 μM to about 500 μM. In still another aspect, the DKP amount can be in an amount of about 50 μM to about 100 μM.

In some embodiments, the concentration of the DKP on a surface of the device exposed to the body is about 1 ng/cm$^2$ to about 200 ng/cm$^2$. In another aspect, the concentration of the DKP on a surface of the device exposed to the body is about 50 ng/cm$^2$.

DESCRIPTION OF THE INVENTION

The present invention relates to the contacting (such as by coating, impregnating, etc.) of one or more surfaces of an implantable medical device with one or more diketopiperazines (DKPs). DKPs can suppress the immune response of a subject against the implanted medical device and can be referred to as immunomodulatory DKPs. By the introduction of DKPs to a surface of an implanted device, the problems associated with immune response against such devices (device failure and patient complications) can be reduced. Without being bound by theory, by coating or contacting an implantable medical device with a DKP, it is believed that the presence of the DKP increases the subject's immune tolerance to the device.

Various embodiments of the present invention include a method to prepare an implantable medical device in a subject by contacting the device with a DKP. Another embodiment is a method for implanting a medical device by implanting a medical device into a subject, wherein a surface of the device comprises a DKP. A further embodiment of the present invention is an implantable medical device, wherein a surface of the device comprises a DKP.

To increase immune tolerance of an implantable medical device and/or for implanting a medical device, the device and/or the surface of the device can be contacted by the diketopiperazine (DKP) of the present invention having the following formula:

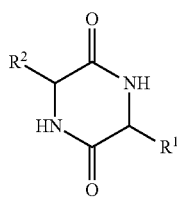

wherein:
$R^1$ and $R^2$, which may be the same or different, each is:
(a) a side chain of an amino acid, wherein the amino acid is glycine, alanine, valine, norvaline, α-aminoisobutyric acid, 2,4-diaminobutyric acid, 2,3-diaminobutyric acid, leucine, isoleucine, norleucine, serine, homoserine, threonine, aspartic acid, asparagine, glutamic acid, glutamine, lysine, hydroxylysine, histidine, arginine, homoarginine, citrulline, phenylalanine, p-aminophenylalanine, tyrosine, tryptophan, thyroxine, cysteine, homocysteine, methionine, penicillamine or ornithine; provided, however, that when $R^1$ is the side chain of asparagine or glutamine, then $R^2$ cannot be the side chain of lysine or ornithine, and when $R^1$ is the side chain of lysine or ornithine, then $R^2$ cannot be the side chain of asparagine or glutamine;
(b) $R^1$ is —$CH_2$—$CH_2$—$CH_2$— or —$CH_2$—$CH(OH)$—$CH_2$— and together with the adjacent ring nitrogen forms proline or hydroxyproline and/or $R^2$ is —$CH_2$—$CH_2$—$CH_2$— or —$CH_2$—$CH(OH)$—$CH_2$— and together with the adjacent ring nitrogen forms proline or hydroxyproline; or
(c) a derivative of a side chain of an amino acid, wherein the amino acid is one of those recited in (a), and the derivatized side chain has:
(i) an —$NH_2$ group replaced by an —$NHR^3$ or —$N(R^3)_2$ group, wherein each $R^3$ may independently be a substituted or unsubstituted alkyl, cycloalkyl, heterocycloalkyl, aryl, alkylaryl, arylalkyl or heteroaryl;
(ii) an —OH group replaced by an —O—$PO_3H_2$ or —$OR^3$ group, wherein each $R^3$ may independently be a substituted or unsubstituted alkyl, cycloalkyl, heterocycloalkyl, aryl, alkylaryl, arylalkyl or heteroaryl;
(iii) a —COOH group replaced by a —$COOR^3$ group, wherein each $R^3$ may independently be a substituted or unsubstituted alkyl, cycloalkyl, heterocycloalkyl, aryl, alkylaryl, arylalkyl or heteroaryl;
(iv) a —COOH group replaced by a —$CON(R^4)_2$ group, wherein each $R^4$ may independently be H or a substituted or unsubstituted alkyl, cycloalkyl, heterocycloalkyl, aryl, alkylaryl, arylalkyl or heteroaryl;
(v) an —SH group replaced by —S—S—$CH_2$—CH($NH_2$)—COOH or —S—S—$CH_2$—$CH_2$—CH($NH_2$)—COOH;
(vi) a —$CH_2$— group replaced by a —CH($NH_2$)— or a —CH(OH)— group;
(vii) a —$CH_3$ group replaced by a —$CH_2$—$NH_2$ or a —$CH_2$—OH group; and/or
(viii) an H which is attached to a carbon atom replaced by a halogen; or a physiologically-acceptable salt thereof.

By "replaced" is meant that, with reference to the formula of an amino acid side chain, the specified group is replaced by the other specified group. For instance, the formula of the isoleucine side chain is —CH($CH_3$)—$CH_2$—$CH_3$. If the terminal —$CH_3$ group is replaced with a —$CH_2$—OH group, then the formula of the resulting derivatized isoleucine side chain would be —CH($CH_3$)—$CH_2$—$CH_2$—OH. As another example, the formula of the alanine side chain is —$CH_3$. If one of the hydrogen atoms is replaced by a chlorine atom, then the resulting derivatized alanine side chain would be —$CH_2$—Cl. Note that the side chain of glycine is —H and, if this H is replaced by a chlorine (or other halogen) atom, the resulting side chain will —Cl, with the chlorine atom attached to the ring carbon (e.g., $R^1$=—Cl)

Preferred are diketopiperazines wherein R', $R^2$ or both is the side chain of aspartic acid or glutamic acid or a derivative of such a side chain wherein the —COOH group is replaced by a —$COOR^3$ group or a —$CON(R^4)_2$ group, wherein $R^3$ and $R^4$ are defined above. Of this group of compounds, most preferred are diketopiperazines comprising the side chains of aspartic acid and alanine (Asp-Ala DKP or DA-DKP), the side chains of glutamic acid and alanine (Glu-Ala DKP or EA-DKP), the side chains of tyrosine and aspartic acid (Tyr-Asp DKP or YD-DKP), the side chains of tyrosine and glutamic acid (Tyr-Glu DKP or YE-DKP) and derivatives of the aspartic acid or glutamic acid side chains of these four diketopiperazines wherein the —COOH group is replaced by a —$COOR^3$ group or a —$CON(R^4)_2$ group, wherein $R^3$ and $R^4$ are defined above.

Also, preferred are diketopiperazines wherein $R^1$ and $R^2$ are both hydrophobic side chains (e.g., the side chain of phenylalanine) or hydrophobic side chain derivatives. By "hydrophobic side chain derivative" is meant that the derivatized side chain which is hydrophobic. In particular, preferred are diketopiperzines wherein $R^1$ and/or $R^2$, which may be the same or different, each is the side chain of glycine, alanine, valine, norvaline, α-aminobutyric acid, leucine, isoleucine, norleucine or phenylalanine, and/or $R^1$ and/or $R^2$ is —$CH_2$—$CH_2$—$CH_2$— and together with the adjacent nitrogen atom(s) form proline. Of this group of compounds, most preferred are the diketopiperazines comprising the side chains of glycine and leucine (Gly-Leu DKP or GL-DKP), proline and phenylalanine (Pro-Phe DKP or PF-DKP), and alanine and proline (Ala-Pro DKP or AP-DKP).

Additional preferred diketopiperazines are those wherein R', $R^2$ or both is the side chain of methionine, the side chain of arginine or a derivative of these side chains. Most preferred of this group is a diketopiperazine wherein $R^1$ is the side chain of methionine and $R^2$ is the side chain of arginine (Met-Arg DKP or MR-DKP).

By "side chain" of an amino acid is meant that portion of the amino acid attached to the common $NH_2$—CH—COOH backbone of all of the amino acids listed above. For instance, the side chain of glycine is —H, the side chain of alanine is —$CH_3$, and the side chain of serine is —$CH_2OH$. By "hydrophobic" is meant a side chain or side chain derivative that is uncharged at physiological pH and is repelled by an aqueous solution.

By "alkyl" is meant a saturated straight-chain or branched hydrocarbon containing 1-10 carbon atoms, preferably 1-6, carbon atoms. "Lower alkyl" means a saturated straight-chain or branched hydrocarbon containing 1-6 carbon atoms.

By "cycloalkyl" is meant a saturated cyclic hydrocarbon containing at least one ring, each ring containing at least three carbon atoms. Preferably, the cycloalkyl contains one ring of 4-8 carbon atoms.

By "heterocycloalkyl" is meant a cycloalkyl having one or more of the ring carbon atoms of at least one of the rings replaced by an O, S or N.

By "aryl" is meant an aromatic group having at least one aromatic ring (e.g., phenyl). By "alkylaryl" is meant a lower alkyl having an H replaced by an aryl (e.g., —$CH_2$—$C_6H_5$ or —$CH_3CH(C_6H_5)CH_3$).

By "arylalkyl" is meant an aryl having an H replaced by a lower alkyl (e.g., —$C_6H_4$—$CH_3$).

By "heteroaryl" is meant an aryl having one or more of the ring carbon atoms of at least one of the rings replaced by an O, S or N.

By "substituted" is meant that the moiety is substituted with one or more substituents selected from the following group: —OH, $NH_2$, —SH, —COOH and/or a halogen atom.

By "halogen" is meant chlorine, fluorine, bromine or iodine. Preferred is chlorine or bromine.

Methods of making diketopiperazines are well known in the art, and these methods may be employed to synthesize the diketopiperazines of the invention. See, e.g., U.S. Pat. Nos. 4,694,081, 5,817,751, 5,990,112, 5,932,579 and 6,555,543, US Patent Application Publication Number 2004/0024180, PCT applications WO 96/00391 and WO 97/48685, and Smith et al., *Bioorg. Med. Chem. Letters*, 8, 2369-2374 (1998), the complete disclosures of which are incorporated herein by reference.

For instance, diketopiperazines can be prepared by first synthesizing dipeptides. The dipeptides can be synthesized by methods well known in the art using L-amino acids, D-amino acids or a combination of D- and L-amino acids. Preferred are solid-phase peptide synthetic methods. Of course, dipeptides are also available commercially from numerous sources, including DMI Synthesis Ltd., Cardiff, UK (custom synthesis), Sigma-Aldrich, St. Louis, Mo. (primarily custom synthesis), Phoenix Pharmaceuticals, Inc., Belmont, Calif. (custom synthesis), Fisher Scientific (custom synthesis) and Advanced ChemTech, Louisville, Ky.

Once the dipeptide is synthesized or purchased, it is cyclized to form a diketopiperazine. This can be accomplished by a variety of techniques. For example, U.S. Patent Application Publication Number 2004/0024180 describes a method of cyclizing dipeptides. Briefly, the dipeptide is heated in an organic solvent while removing water by distillation. Preferably, the organic solvent is a low-boiling azeotrope with water, such as acetonitrile, allyl alcohol, benzene, benzyl alcohol, n-butanol, 2-butanol, t-butanol, acetic acid butylester, carbon tetrachloride, chlorobenzene chloroform, cyclohexane, 1,2-dichlorethane, diethylacetal, dimethylacetal, acetic acid ethylester, heptane, methylisobutylketone, 3-pentanol, toluene and xylene. The temperature depends on the reaction speed at which the cyclization takes place and on the type of azeotroping agent used. The reaction is preferably carried out at 50-200° C., more preferably 80-150° C. The pH range in which cyclization takes place can be easily determined by the person skilled in the art. It will advantageously be 2-9, preferably 3-7. When one or both of the amino acids of the dipeptide has, or is derivatized to have, a carboxyl group on its side chain (e.g., aspartic acid or glutamic acid), the dipeptide is preferably cyclized as described in U.S. Pat. No. 6,555,543. Briefly, the dipeptide, with the side-chain carboxyl still protected, is heated under neutral conditions. Typically, the dipeptide will be heated at from about 80° C. to about 180° C., preferably at about 120° C. The solvent will be a neutral solvent. For instance, the solvent may comprise an alcohol (such as butanol, methanol, ethanol, and higher alcohols, but not phenol) and an azeotropic co-solvent (such as toluene, benzene, or xylene). Preferably, the alcohol is butan-2-ol, and the azeotropic co-solvent is toluene. The heating is continued until the reaction is complete, and such times can be determined empirically. Typically, the dipeptide will be cyclized by refluxing it for about 8-24 hours, preferably about 18 hours. Finally, the protecting group is removed from the diketopiperazine. In doing so, the use of strong acids (mineral acids, such as sulfuric or hydrochloric acids), strong bases (alkaline bases, such as potassium hydroxide or sodium hydroxide), and strong reducing agents (e.g., lithium aluminum hydride) should be avoided, in order to maintain the chirality of the final compound.

Dipeptides made on solid phase resins can be cyclized and released from the resin in one step. See, e.g., U.S. Pat. No. 5,817,751. For instance, the resin having an N-alkylated dipeptide attached is suspended in toluene or toluene/ethanol in the presence of acetic acid (e.g., 1%) or triethylamine (e.g., 4%). Typically, basic cyclization conditions are preferred for their faster cyclization times.

To prepare the diketopiperazine of formula I wherein the amino acid side chains are derivatized, amino acid derivatives can be used in the synthesis of the dipeptides, the dipeptides can be derivatized and/or the diketopiperazines can be derivatized, as is known in the art. See, e.g., those references cited above.

Other methods of cyclizing dipeptides and of making diketopiperazines are known in the art and can be used in the preparation of diketopiperazines useful in the practice of the invention. See, e.g., those references listed above. In addition, many diketopiperazines suitable for use in the present invention can be made as described below from proteins and peptides. Further, diketopiperazines for use in the practice of the invention can be obtained commercially from, e.g., DMI Synthesis Ltd., Cardiff, UK (custom synthesis).

The diketopiperazines of formula I include all possible stereoisomers than can be obtained by varying the configuration of the individual chiral centers, axes or surfaces. In other words, the diketopierazines of formulas I and II include all possible diastereomers, as well as all optical isomers (enantiomers).

The physiologically-acceptable salts of the diketopiperazines of the invention may also be used in the practice of the invention. Physiologically-acceptable salts include conventional non-toxic salts, such as salts derived from inorganic acids (such as hydrochloric, hydrobromic, sulfuric, phosphoric, nitric, and the like), organic acids (such as acetic, propionic, succinic, glycolic, stearic, lactic, malic, tartaric, citric, glutamic, aspartic, benzoic, salicylic, oxalic, ascorbic acid, and the like) or bases (such as the hydroxide, carbonate or bicarbonate of a pharmaceutically-acceptable metal cation or organic cations derived from N,N-dibenzylethylenediamine, D-glucosamine, or ethylenediamine). The salts are prepared in a conventional manner, e.g., by neutralizing the free base form of the compound with an acid.

It has been found that diketopiperazines suitable for use in the present invention are present in some commercially-available intravenous pharmaceutical compositions containing albumin, immunoglobulin and erythropoietin. The diketopiperazines present in these pharmaceutical preparations are formed by the heating steps often used in the manufacture of these pharmaceutical compositions. The heating results in cleavage and cyclization of the two N-terminal and/or two C-terminal amino acids of the proteins to form diketopiperazines.

Accordingly, diketopiperazines for use in the present invention can be prepared by heating solutions of albumin, immunoglobulin, erythropoietin and other proteins and peptides. For example, a solution of albumin, immunoglobulin, erythropoietin or another protein or peptide in phosphate buffer at neutral pH is prepared. Preferably, the solution is a concentrated solution (e.g., about 100-500 mM) to achieve protonation of the N-terminal and/or C-terminal amino acid. The solution is heated at 60° C. for from about 2 hours to several days, preferably about 4 days, to cause formation of the diketopiperazines. Denaturation of the protein should, preferably, be avoided. This can be accomplished by using shorter times and/or by adding caprylic acid or N-acetyl tryptophan at about 0.02 M for each.

Diketopiperazines for use in the present invention can also be prepared by contacting a solution of albumin, immunoglobulin, erythropoietin or another protein or peptide with an enzyme that can cleave the two N-terminal amino acids from the protein or peptide (e.g., dipeptidyl peptidases) or an enzyme that can cleave the two C-terminal amino acids from the protein or peptide (e.g., carboxypeptidases). Suitable dipeptidyl peptidases and carboxypeptidases are available commercially from, e.g., Sigma. The reaction should be conducted at pH 6-8, preferably in a buffer, such as phosphate buffer, at a temperature high enough to speed the reaction but not so high that the protein is denatured (e.g., 37° C.).

The amino acid sequences of numerous proteins and peptides are known, and a protein or peptide with the desired N-terminal and/or C-terminal sequence can be chosen to give the desired diketopiperazine(s) using either method. Also, peptides with a desired sequence can be synthesized by well known methods and used.

The diketopiperazines can be purified from solutions containing them, including from the commercially-available pharmaceutical compositions comprising albumin, immunoglobulin and erythropoietin, by well known methods, such as size-exclusion chromatography (e.g., Centricon filtration), affinity chromatography (e.g., using a column of beads having attached thereto an antibody or antibodies directed to the desired diketopiperazine(s) or an antibody or antibodies directed to the truncated protein or peptide), anion exchange or cation exchange. The purified diketopiperazines can be used and incorporated into pharmaceutical compositions as described above.

A DA-DKP composition of the present invention can be prepared from solutions containing DA-DKP, including from the commercially-available pharmaceutical compositions comprising albumin, such as human serum albumin, by well known methods, such as ultrafiltration, chromatography (size-exclusion chromatography (e.g., Centricon filtration), affinity chromatography (e.g., using a column of beads having attached thereto an antibody or antibodies directed to the desired diketopiperazine(s) or an antibody or antibodies directed to the truncated protein or peptide), anion exchange or cation exchange), sucrose gradient centrifugation, chromatography, salt precipitation, or sonication, that will remove some or all of the albumin in the solution. The resultant DA-DKP-containing composition can be used and incorporated into compositions used to coat, impregnate or cover the implantable medical devices of the present invention.

Using ultrafiltration as a separation method, a human serum albumin composition can be passed over an ultrafiltration membrane having a molecular weight cut-off that retains the albumin while the DA-DKP passes into the resulting filtrate or fraction. This filtrate may comprise components having molecular weights less than about 50 kDA, less than about 40 kDa, less than 30 kDa, less than about 20 kDa, less than about 10 kDa, less than about 5 kDa, less than about 3 kDa. Preferably, the filtrate comprises components having molecular weights less than about 5 Da (also referred to as "<5000 MW"). This <5000 MW fraction or filtrate contains DA-DKP which is formed after the dipeptide aspartate-alanine is cleaved from albumin and subsequently cyclized into the diketopiperazine.

Implantable medical devices of the present invention are devices which can be implanted into a subject. For example, such devices can be a graft, a catheter, stent, prosthetic, implant (such as a breast implant), pump, tubes, pins, rods, screws, brace, plates or pace maker. Stents can include but are not limited cardiac stents and artery stents (for example for use in widening arteries and to improve blood flow), and birth control stents (such as Essure®). Prosthetics can include but are not limited to artificial hip(s), artificial knee(s) or artificial ankle(s). Pumps can include but are not limited to insulin pumps.

The implantable medical devices of the present invention can be composed of one or more various materials. For example, the material can be metal, steel, titanium, glass, polymers, plastics or ceramics.

The diketopiperazines of the invention can be adhered to, impregnated into or coated onto the surface of the implantable medical devices. For example, an implanted medical device can be contacted with a DKP containing solution, wherein the solution adheres to or impregnates into or coats the implantable medical device. The concentration of the DKP that adheres to or is coated onto the surface of the implanted medical device can be in a range with a lower endpoint of about 1 µM, about 5 µM, about 10 µM, about 20 µM, about 30 µM, about 40 µM, about 50 µM, about 60 µM, about 70 µM, about 80 µM, about 90 µM, about 100 µM, about 110 µM, about 120 µM, about 130 µM, about 140 µM, about 150 µM, about 160 µM, about 170 µM, about 180 µM, about 190 µM, or about 200 µM. In addition, the concentration of the DKP that adheres to or is coated onto the surface of the implanted medical device can be in a range with an upper endpoint of about 500 µM, about 475 µM, about 450 µM, about 425 µM, about 400 µM, about 375 µM, about 350 µM, about 325 µM, about 320 µM, about 310 µM, about 300 µM, about 290 µM, about 280 µM, about 270 µM, about 260 µM, about 250 µM, about 240 µM, about 230 µM, about 220 µM, or about 210 µM.

In a further embodiment of the present invention, the concentration of the DKP on a surface of a medical device that is exposed to the body when implanted can be in a range with a lower endpoint of about 1 ng/cm$^2$, about 5 ng/cm$^2$, about 10 ng/cm$^2$, about 15 ng/cm$^2$, about 20 ng/cm$^2$, about 25 ng/cm$^2$, about 30 ng/cm$^2$, about 35 ng/cm$^2$, about 40 ng/cm$^2$, about 45 ng/cm$^2$, about 50 ng/cm$^2$, about 55 ng/cm$^2$, about 60 ng/cm$^2$, about 65 ng/cm$^2$, about 70 ng/cm$^2$, about 75 ng/cm$^2$, about 80 ng/cm$^2$, about 85 ng/cm$^2$, about 90 ng/cm$^2$, about 95 ng/cm$^2$, or about 100 ng/cm$^2$. Preferably, the concentration of the DKP on a surface of a medical device that is exposed to the body when implanted is about 50 ng/cm². In addition, the concentration of the DKP on a surface of a medical device that is exposed to the body when implanted can be in a range with an upper endpoint of about 200 ng/cm², about 195 ng/cm², about 190 ng/cm², about 185 ng/cm², about 180 ng/cm², about 175 ng/cm², about 170 ng/cm², about 165 ng/cm², about 160 ng/cm², about 155 ng/cm², about 150 ng/cm², about 145 ng/cm², about 140 ng/cm², about 135 ng/cm², about 130 ng/cm², or about 125 ng/cm².

Subjects of the present invention can be a mammal, such as a rabbit, goat, dog, cat, horse or human. Preferably, the subject is a human.

As used herein, "a" or "an" means one or more.

As used herein, "comprises" and "comprising" include within their scope all narrower terms, such as "consisting essentially of" and "consisting of" as alternative embodiments of the present invention characterized herein by "comprises" or "comprising". In regard to use of "consisting essentially of", this phrase limits the scope of a claim to the specified steps and materials and those that do not materially affect the basic and novel characteristics of the invention disclosed herein.

Additional objects, advantages and novel features of the present invention will become apparent to those skilled in the art by consideration of the following non-limiting examples. The following experimental results are provided for purposes of illustration and are not intended to limit the scope of the invention.

EXAMPLES

Example 1

This example shows the results of an analysis of biofilms on extracted orthopedic devices to determine if the presence of a diketopiperazine is correlated with bacterial colonization. Bacteria use small molecular weight N-acylhomoserine lactones and diketopiperazines to initiate biofilm formation and regulate colony growth. An Aspartate, Alanine-Diketopiperazine (DA-DKP) formed by the cleavage and cyclization of the N-terminal amino acids of human serum albumin has previously been demonstrated to be immunomodulatory for memory but not naive human T lymphocytes.

Methods:

This study was an institutional review board (IRB) approved study. Twenty two patients undergoing hardware removal were enrolled. The removed orthopedic devices were stripped of surface biofilm using methanol/ammonium formate. The ≤3 kD MW material was collected and diketopiperazine levels analyzed using anion exchange high pressure liquid chromatography coupled to negative electrospray ionization mass spectrometry.

Results:

The thirty-three patients ranged in age from 6 to 91 years, with a mean of 54. There were fifteen males and eighteen females. Ten devices were reported by the clinical laboratory to be culture positive. In five cases the main organism was *Staphylococcus*. In one of the three cases *Bacteroides* and *Streptococcus* species were also isolated. In all thirty-three cases detectable amounts of DA-DKP were identified with a mean level of 120 ng/ml. Higher amounts of DA-DKP (9.75-235 ng/ml) were detected in the culture positive devices versus the culture negative (1.78-34.7 ng/ml). In addition, one device removed from a case with osteomyelitis had a DA-DKP content of 3,063 ng/ml. (see Table 1).

Conclusion:

DA-DKP is an important immune modulator in biofilm formation on orthopedic implants. Its presence in biofilms found on extracted orthopedic devices suggests innate physiologic mechanisms conferring tolerance to the implanted device possibly correlated to the presence of inflammation/rejection reactions.

TABLE 1

Study Group DA-DKP amounts

| Age of subject | Sex of subject F = female M = male | Device Removed | Culture Results | Concentration of DA-DKP ng/ml |
|---|---|---|---|---|
| 73 | F | Pin (hip) | None | 4.63 |
| 66 | F | Rod + Screws (hip) | Negative | 19.7 |
| 89 | F | Rod + Screws (hip) | Staph (positive) | 87.0 |
| 74 | M | Staple (knee) | None | 3.03 |
| 67 | F | Septic hip prosth. | *Staph aureus* | 84.8 |
| 44 | M | Plate (clavicle) | None | 2.40 |
| 45 | F | Rod + Screws (spine) | Negative | 30.9 |
| 87 | F | Screws (hip arthritis) | None | 19.9 |
| 33 | M | Rod + Screws (knee) | None | 6.03 |
| 45 | M | Rod + Screws (ulna) | None | 9.05 |
| 31 | F | Rod + Screws (ankle) | Bacteroides + Strep | 53.7 |
| 52 | F | Brace + Screws (tibia) | None | 9.02 |
| 58 | F | Screws (femur) | Staph (positive) | 28.4 |
| 74 | M | Brace (clavicle) | Negative | 7.02 |
| 6 | M | Plate + Screws | None | 22.4 |
| 60 | F | Rod (osteomyelitis tibia) | Negative | 3,063 |
| 58 | F | Hip Prosth. | Negative | 23.0 |
| 66 | F | Rod (femoral) | Staph + Strep | 235 |
| 45 | M | Rod + Screws (tibia) | Gram+ | 12.9 |
| 55 | M | Nails (femoral) | Gram+ | 70.4 |
| 54 | F | Ankle Prosth. | Negative | 34.7 |
| 24 | M | Screws (tibia) | Gram+ | 9.75 |
| 91 | F | Screws (hip) | None | 3.91 |
| 44 | M | Plate + Screws (ankle) | None | 14.2 |
| 46 | F | Screws (ankle) | None | 9.32 |
| 24 | M | Screws (femur) | *Staph aureus* | 53.1 |

TABLE 1-continued

Study Group DA-DKP amounts

| Age of subject | Sex of subject F = female M = male | Device Removed | Culture Results | Concentration of DA-DKP ng/ml |
|---|---|---|---|---|
| 68 | F | Knee Prosth. | Negative | 1.78 |
| 56 | F | Screws (knee) | None | 3.41 |
| 41 | F | Brace + Screws (ankle) | Yeast | 20.4 |
| 61 | M | Screws (femur) | Negative | 4.21 |
| 34 | M | Plate + Screws (radius) | Negative | 9.78 |
| 77 | M | Plate + Rod (hip) | None | 2.13 |
| 28 | M | Plates + Screw (ankle) | None | 12.7 |

Example 2

Isolation and characterization of peptides and proteins from endotracheal tubes. The results of this example further demonstrate that DKPs form on implantable medical devices such as endotracheal tubes, when they are implanted within a subject. The presence of the DKPs on these tubes helps the subject to confer tolerance to the tubes. This again demonstrates the unique finding of coating implantable medical devices, such as entracheal tubes, with DPKs prior to implantation so as to increase the subject's immune tolerance and/or to decrease a subject's inflammatory response to the tube.

Endotracheal tubes discarded from mechanically ventilated trauma patients are collected into sterile biohazard pouches and transported immediately to the Trauma Research Lab. As controls for the absence of biofilms, discarded endotracheal tubes form surgical patients that were only used for a few hours during surgery were used.

Method

Biofilm and/or mucus is stripped from the proximal ends of endotracheal tubes by placing in a sterile centrifuge tube containing 1-2 ml of chromatography each analysis buffer consisting of methanol 60% plus 50 mM ammonium formate 40% with extensive washing using a pipette and agitation on a vortexer. After the biofilm is stripped from the endotracheal tube, the sediment is pelleted by centrifugation and frozen for later analysis of bacterial content. The biofilm supernatant is collected for analysis of protein and large molecular width peptides. An aliquot of the biofilm supernatant is placed in an ultrafiltration spin column (Vivaspin 500, 3,000 MWCO, Sartorius, Hannover, Germany) for centrifugation at 15,000×g. The filtrate is collected for analysis of <3 kD molecular weight peptides.

Supernatants containing higher molecular weight material are analyzed by high performance liquid chromatography (HPLC, Waters, Milford, Mass., USA) coupled to positive electrospray ionization time of flight mass spectrometry (+ESI-TOF MS, Micromass, UK). Each supernatant is diluted 1:10 with dH$_2$O. 10 μL of each sample is injected onto a YMC-Pack Protein-PR, 150 mm×4.6 mm, 5 u, HPLC column heated at 50° C. (Waters, Milford, Mass., USA) using a 20 minute linear gradient method used water/0.1% trifluoroacetic acid (A) and acetonitrile/0.1% TFE (B). The output of the HPLC is split 1:20 (v:v) and injected into the mass spectrometer with a scan range of 500 to 3500 m.z, cone voltage of 30 eV, source temperature of 100° C., and gas temperature of 250° C. Albumin (a molecular standard) elutes at 8.15 minutes and is visualized as a charge envelope from 1100 to 2500 m/z representing +44 to +26 charges. The spectrum is the deconvolved to the uncharged parent mass using MaxEnt 1 (Micromass, UK). The parent mass spectrum is then integrated and relative proportions of each species were calculated.

50 μl of each of the <3000-Da filtrate fractions of bioflim supernatant is injected into high performance liquid chromatography (HPLC, 2795 system, Waters, Mass.) coupled to a mass spectrometer (LCT-TOF, Micromass, UK), and quantified using a storage anion exchange column (Supelcosil, SAX1 250 mm×4.6 mm, Supelco) and a 70:30 v/v methanol/water with 25 mM ammonium acetate (Sigma Aldrich, St. Lois, Mo.) as the mobile phase in an isocratic mode at 1 ml/min. The output of the HPLC is split 1:20 (v/v) and injected into the mass spectrometer using negative electrospray ionization (−ESI MS) with a scan ranges of 80-1000 m/z, cone voltage of 30 eV, source temperature of 100° C. and a gas temperature of 250° C. DA-DKP, as a molecular standard, is measure by monitoring the mass 185 in time which corresponds to DA-DKP minus a single proton (−H+). DA-DKP elutes at 5.8 mins and is quantified by integrating the area under the curve. The area was compared with a standard curve derived from synthetic DA-DKP standard (DMI Synthesis, Newport, Wales) of known concentrations (5000 ng/ml, 1000 ng/ml, 200 ng/ml, 40 ng/ml, 8 ng/ml). The calibration curve was found to be very linear in this range within R2 of 0.99998.

The concentration of DKP on over 100 endothracheal tubes as detected by the method described above is presented in Table 2. The DKP concentration ([DKP]) provided on Table 2 has already been adjusted per volume added to dissolve biofilm. The following are indicated on Table 2:

ID #: Subject identification number
Sex: Subject's sex either male (M) or female (F)
Age: Age in years of the subject
[DKP] ng/ml: The DKP concentration in ng/ml already adjusted per volume added to dissolve biofilm
Bacteria identified: Type of bacteria detected on endotracheal tube
Vent Days: The number of days the endotracheal tube was implanted with the subject Protein identified: The proteins that were determined on the endotracheal tube
AIS: Abbreviated injury score/scale, with a score of 1 being a minor injury, 2=moderate, 3=serious, 4=severe, 5=critical, 6=maximum, 9=not further specified.
ISS: Injury severity score, assesses trauma severity and correlates with mortality, morbidity and hospitalization time after trauma.
GCS: Glasgow coma score/scale-neurological scale to help assess the status of the central nervous system and used acutely to grade the severity of a subject's trauma and mental function.
GOS: Glasgow outcome score/scale (R=rehabilitation; L=long term acute care; 1=dead; 5=good recovery)—a 5 point score given to victims of traumatic brain injury at some point in their recovery.

TABLE 2

DKP Concentration on Endotracheal Tubes

| ID # | Sex | Age | [DKP] ng/ml | Bacteria | Vent Days | Proteins ID | AIS | ISS | GCS | GOS |
|---|---|---|---|---|---|---|---|---|---|---|
| 18 | M | 25 | 150.06 | | 8 | PRP1, HIG2, AT5G1 | 2 | 38 | 15 | 5 |
| 24 | M | 47 | 607.73 | S. pneumon MRSA | 11 | Defensin 1, 2, 3 LL-37, Lysozyme C | 3 | 20 | 15 | R |
| 25 | M | 90 | <20 | | 3 | Defensin 1, 2, 3 LL-37 | 3 | 14 | 6 | 1 |
| 28 | F | 22 | <20 | | 1 | Defensin 1, 2, 3 LL-37 | 3 | 21 | 7 | R |
| 30 | F | 55 | 1,071.55 | Enterob. Sakazakii | 4 | | 2 | 17 | 3 | R |
| 30-2 | F | 55 | <20 | Enterob. Sakazakii | 4 | | 2 | 17 | 3 | R |
| 31 | M | 60 | 1,402.85 | | 9 | S10A8 | 3 | 10 | 15 | 5 |
| 34 | M | 20 | <20 | H. influenza | 30 | | 5 | 45 | 3 | R |
| 35 | F | 71 | 116.29 | | 7 | | 4 | 30 | 6 | L |
| 36 | M | 46 | 1,580.08 | Pneumothorax | 11 | | 3 | 34 | 9 | R |
| 36-2 | M | 46 | <20 | Pneumothorax | 11 | | 3 | 34 | 9 | R |
| 39 | M | 58 | <20 | | 5 | | 4 | 29 | 15 | L |
| 41 | M | 35 | 72.53 | K. oxytoca S. aureus | 20 | | 3 | 43 | 3 | L |
| 44 | M | 35 | <20 | | 8 | | 4 | 25 | 4 | 5 |
| 45 | M | 17 | 34.09 | S. marcesens | 3 | | 1 | 21 | 3 | 5 |
| 50 | M | 76 | 362.29 | | 1 | | 3 | 22 | | |
| 52 | M | 34 | 159.56 | | <1 | | 2 | 17 | 12 | R |
| 53 | M | 21 | 156.85 | | <1 | | 3 | 14 | 6 | 1 |
| 58 | M | 25 | <20 | | 36 | | 5 | 29 | 15 | L |
| 60 | M | 15 | 124.82 | | 1 | | 1 | 41 | | 5 |
| 70 | M | 28 | 104.63 | | 4 | | 3 | 26 | 3 | R |
| 79 | M | 73 | 33.48 | K. oxytoca | 8 | | | | 4 | L |
| 87 | M | 49 | 79.92 | | | | | | | |
| 90 | F | 56 | 103.79 | | | | | | | |
| 96 | F | 49 | 637.7 | | | | | | | |
| 97 | M | 30 | 1,752.89 | | | | | | | |
| 98 | F | 24 | 952.71 | | | | | | | |
| 102 | M | 32 | 1,311.48 | | | | | | | |
| 106 | F | 80 | 1,083.15 | | | | | | | |
| 108 | F | 59 | 2,648.23 | | | | | | | |
| 109 | M | 20 | 629.67 | | | | | | | |
| 114 | M | 76 | 379.51 | | | | | | | |
| 121 | F | 84 | 2,325.85 | | | | | | | |
| 123 | M | 15 | 8,009.14 | | | | | | | |
| 129 | M | 27 | 500.95 | | | | | | | |
| 131 | F | 65 | 16,194.74 | | | | | | | |
| 132 | M | 32 | 282.84 | | | | | | | |
| 133 | F | 48 | 480.59 | | | | | | | |
| 138 | M | 49 | 137.37 | | | | | | | |
| 140 | F | 81 | 567.2 | | | | | | | |
| 143 | M | 28 | 426.93 | | | | | | | |
| 145 | M | 68 | 1,655.73 | | | | | | | |
| 149 | M | 21 | 58.68 | | | | | | | |
| 149-2 | M | 21 | 749.03 | | | | | | | |
| 150 | M | 31 | 111.68 | | | | | | | |
| 151 | M | 50 | 389.23 | | | | | | | |
| 152 | M | 25 | 134.8 | | | | | | | |
| 153 | F | 51 | 272.45 | | | | | | | |
| 156 | M | 29 | 25.45 | | | | | | | |
| 157 | F | 18 | 634.13 | | | | | | | |
| 158 | M | 51 | 2,183.93 | | | | | | | |
| 161 | M | 77 | 386.28 | | | | | | | |
| 161-2 | M | 77 | 691.98 | | | | | | | |
| 162 | M | 18 | 364.63 | | | | | | | |
| 163 | M | 63 | 107.4 | | | | | | | |
| 164 | F | 15 | 69.15 | | | | | | | |
| 166 | F | 18 | 856.74 | | | | | | | |
| 169 | F | 30 | <20 | | | | | | | |
| 170 | M | 73 | 368.9 | | | | | | | |
| 178 | M | 53 | 48.55 | | | | | | | |
| 179 | M | 25 | <20 | | | | | | | |
| 182 | M | 67 | 1059.7 | | | | | | | |
| 182-2 | M | 67 | 255.73 | | | | | | | |

TABLE 2-continued

DKP Concentration on Endotracheal Tubes

| ID # | Sex | Age | [DKP] ng/ml | Bacteria | Vent Days | Proteins ID | AIS | ISS | GCS | GOS |
|---|---|---|---|---|---|---|---|---|---|---|
| 183 | M | 36 | 279.76 | | | | | | | |
| 184 | M | 37 | <20 | | | | | | | |
| 190 | M | 34 | 624.44 | | | | | | | |
| 191 | M | 29 | 2,207.58 | | | | | | | |
| 191-2 | M | 29 | 798.37 | | | | | | | |
| 192 | M | 66 | <20 | | | | | | | |
| 195 | M | 28 | 2,608.52 | | | | | | | |
| 196 | F | 23 | <20 | | | | | | | |
| 198 | M | 35 | 404.87 | | | | | | | |
| 200 | M | 33 | 816.38 | | | | | | | |
| 202 | M | 67 | <20 | | | | | | | |
| 203 | M | 50 | 112.64 | | | | | | | |
| 204 | | | 1,290.96 | | | | | | | |
| 205 | | | 2,108.70 | | | | | | | |
| 206 | | | 656.8 | | | | | | | |
| 208 | | | <20 | | | | | | | |
| 209 | | | 276.96 | | | | | | | |
| 210 | | | 76.19 | | | | | | | |
| 211 | | | 76.98 | | | | | | | |
| 212 | | | <20 | | | | | | | |
| 212-2 | | | 505.63 | | | | | | | |
| 213 | | | 218.41 | | | | | | | |
| 215 | | | 503.16 | | | | | | | |
| 215-2 | | | 322.54 | | | | | | | |
| 216 | | | 163.25 | | | | | | | |
| 219 | | | 12,019.74 | | | | | | | |
| 221 | | | 177.19 | | | | | | | |
| 222 | | | 155.14 | | | | | | | |
| 225 | | | 247.88 | | | | | | | |
| 228 | | | 190.86 | | | | | | | |
| 229 | | | 92.4 | | | | | | | |
| 231 | | | 243.68 | | | | | | | |
| 233 | | | 72.03 | | | | | | | |
| 234 | | | 22.96 | | | | | | | |
| 235 | | | 356.11 | | | | | | | |
| 235-2 | | | 68.11 | | | | | | | |
| 237 | | | 509.7 | | | | | | | |
| 239 | | | 1,620.48 | | | | | | | |
| Surg 001 | | | 2,648.55 | | <1 | | | | | |
| Surg 002 | | | 500.22 | | <1 | | | | | |
| Surg 003 | | | 56.74 | | <1 | | | | | |
| Surg 004 | | | 505.67 | | <1 | | | | | |
| Surg 005 | | | <20 | | <1 | | | | | |
| Surg 92 | F | 83 | 89.23 | | | | | | | |
| Surg 92-2 | F | 83 | 67.87 | | | | | | | |
| R 111 | | | 2235.63 | | | | | | | |
| R 113 | | | 1216.05 | | | | | | | |

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

What is claimed:

1. A method to prepare an implantable medical device for implantation in a subject, comprising contacting the device with a diketopiperazine comprising the side chains of aspartic acid and alanine (DA-DKP).

2. The method of claim 1, wherein the implantable medical device is selected from the group consisting of a graft, catheter, stent, prosthetic, breast implant, pump, tube, pin, rod, screw, brace, plate and pace maker.

3. The method of claim 1, wherein the implantable medical device is composed of a material selected from the group consisting of metal, steel, titanium, glass, polymers, plastics, and ceramics.

4. The method of claim 1, wherein the DA-DKP is adhered to, impregnated into, or coated onto the surface of the implantable medical device.

5. The method of claim 1, wherein the implantable medical device is contacted with a solution comprising DA-DKP, wherein the solution adheres to the implantable medical device.

6. The method of claim 1, wherein the DA-DKP is in an amount of about 1 μM to about 500 μM.

7. The method of claim 1, wherein the DA-DKP is in an amount of about 50 μM to about 100 μM.

8. The method of claim 1, wherein the concentration of the DA-DKP on a surface of the implantable medical device exposed to the body is about 1 ng/cm$^2$ to about 200 ng/cm2.

9. The method of claim 1, wherein the concentration of the DA-DKP on a surface of the implantable medical device exposed to the body is about 50 ng/cm$^2$.

10. The method of claim 1, wherein the subject is a mammal.

11. A method for implanting a medical device comprising implanting a medical device into a subject, wherein a surface of the device comprises a diketopiperazine comprising the side chains of aspartic acid and alanine (DA-DKP).

12. The method of claim 11, wherein the implantable medical device is selected from the group consisting of a graft, catheter, stent, prosthetic, breast implant, pump, tube, pin, rod, screw, brace, plate and pace maker.

13. The method of claim 11, wherein the implantable medical device is composed of a material selected from the group consisting of metal, steel, titanium, glass, polymers, plastics, and ceramics.

14. The method of claim 11, wherein the DKP is adhered to, impregnated into, or coated onto the surface of the implantable medical device.

15. The method of claim 11, wherein the implantable medical device is contacted with a solution comprising DA-DKP, wherein the solution adheres to the implantable medical device.

16. The method of claim 11, wherein the DA-DKP is in an amount of about 50 μM to about 100 μM.

17. The method of claim 11, wherein the concentration of the DA-DKP on a surface of the implantable medical device exposed to the body is about 1 ng/cm$^2$ to about 200 ng/cm$^2$.

18. The method of claim 11, wherein the concentration of the DA-DKP on a surface of the implantable medical device exposed to the body is about 50 ng/cm$^2$.

19. The method of claim 10, wherein the mammal is human.

20. The method of claim 1, wherein the subject's immune tolerance to the device is increased by the presence of the DA-DKP.

* * * * *